US007708014B2

(12) United States Patent
Yamashita et al.

(10) Patent No.: US 7,708,014 B2
(45) Date of Patent: May 4, 2010

(54) INHALATION DEVICE FOR TRANSPULMONARY ADMINISTRATION

(75) Inventors: Chikamasa Yamashita, Naruto (JP); Hitoshi Matsushita, Tokushima (JP); Shigeru Ibaragi, Tokushima (JP); Akitsuna Akagi, Naruto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 546 days.

(21) Appl. No.: 10/538,176

(22) PCT Filed: Dec. 12, 2003

(86) PCT No.: PCT/JP03/15943

§ 371 (c)(1),
(2), (4) Date: Jun. 9, 2005

(87) PCT Pub. No.: WO2004/054647

PCT Pub. Date: Jul. 1, 2004

(65) Prior Publication Data

US 2006/0169280 A1 Aug. 3, 2006

(30) Foreign Application Priority Data

Dec. 13, 2002 (JP) ............................ 2002-362754

(51) Int. Cl.
*A61M 15/00* (2006.01)
*A61M 11/00* (2006.01)

(52) U.S. Cl. ............................ 128/203.15; 128/203.21; 128/203.22; 128/203.23; 128/204.26; 128/205.21

(58) Field of Classification Search ............ 128/200.14, 128/200.23, 200.22, 203.12, 203.15, 203.21, 128/204.14, 204.23, 204.26, 205.21; 239/357, 239/326, 349, 354; 222/187, 383.1, 634
See application file for complete search history.

(56) References Cited

U.S. PATENT DOCUMENTS

| | | | | | |
|---|---|---|---|---|---|
| 3,888,253 | A | | 6/1975 | Watt et al. | |
| 3,998,226 | A | * | 12/1976 | Harris | 128/203.15 |
| 4,064,878 | A | | 12/1977 | Lundquist | |
| 4,105,027 | A | | 8/1978 | Lundquist | |
| 4,338,931 | A | | 7/1982 | Cavazza | |
| 5,301,666 | A | * | 4/1994 | Lerk et al. | 128/203.15 |
| 5,435,282 | A | * | 7/1995 | Haber et al. | 128/200.16 |

(Continued)

FOREIGN PATENT DOCUMENTS

CN 1074381 A 7/1993

(Continued)

OTHER PUBLICATIONS

Notification of First Office Action in corresponding Chinese Patent Application No. 200380106027.9 dated Feb. 22, 2008.

*Primary Examiner*—Justine R Yu
*Assistant Examiner*—Clinton Ostrup
(74) *Attorney, Agent, or Firm*—Finnegan, Henderson, Farabow, Garrett & Dunner, L.L.P.

(57) ABSTRACT

An inhalation device for transpulmonary administration comprises: a chamber (16) for containing a pharmaceutical composition which is pulverized into fine particles by an air-generated impact for dispersal in air; an air inlet flow path (2) for introducing to the chamber (16) outside air to apply the air-generated impact to the pharmaceutical composition and for injecting the outside air toward the pharmaceutical composition; an inhalation flow path (1) for inhaling the pulverized pharmaceutical composition; a housing (9) for accommodating the chamber (16), the air inlet flow path (2), and the inhalation flow path (1); a mouthpiece (10) provided at one end of the housing (9), the mouthpiece (9) being provided with a mouth-side flow path (11) which communicates with the inhalation flow path (1), and an auxiliary flow path (12).

13 Claims, 22 Drawing Sheets

U.S. PATENT DOCUMENTS

| | | | | |
|---|---|---|---|---|
| 5,435,297 | A | 7/1995 | Klein | |
| 5,497,765 | A * | 3/1996 | Praud et al. | 128/200.23 |
| 5,577,497 | A * | 11/1996 | Mecikalski et al. | 128/203.15 |
| 5,654,007 | A * | 8/1997 | Johnson et al. | 424/489 |
| 5,758,637 | A * | 6/1998 | Ivri et al. | 128/200.16 |
| 5,785,049 | A * | 7/1998 | Smith et al. | 128/203.15 |
| 5,964,416 | A * | 10/1999 | Jaeger et al. | 239/333 |
| 5,993,421 | A * | 11/1999 | Kriesel | 604/132 |
| 6,039,042 | A * | 3/2000 | Sladek | 128/200.23 |
| 6,186,141 | B1 | 2/2001 | Pike et al. | |
| 6,273,086 | B1 | 8/2001 | Ohki et al. | |
| 6,367,473 | B1 | 4/2002 | Käfer | |
| 6,615,826 | B1 * | 9/2003 | Gabrio et al. | 128/200.23 |
| 6,712,070 | B2 * | 3/2004 | Drachmann et al. | 128/203.12 |
| 2001/0020472 | A1 * | 9/2001 | Horlin | 128/203.15 |
| 2001/0027790 | A1 * | 10/2001 | Gieschen et al. | 128/203.15 |
| 2003/0101995 | A1 * | 6/2003 | Yamashita et al. | 128/203.15 |

FOREIGN PATENT DOCUMENTS

| | | | |
|---|---|---|---|
| EP | 1 106 196 | A2 | 6/2001 |
| FR | 2 313 946 | | 1/1977 |
| FR | 2 454 813 | A | 11/1980 |
| GB | 2 340 758 | A1 | 3/2000 |
| JP | 11-221280 | | 8/1999 |
| WO | WO 91/06333 | | 5/1991 |
| WO | WO 95/31238 | | 11/1995 |
| WO | WO 01/26720 | A1 | 4/2001 |

* cited by examiner (a)

(b)

INHALATION DEVICE FOR TRANSPULMONARY ADMINISTRATION

TECHNICAL FIELD

The present invention relates to a self-inhaling type inhalation device for transpulmonary administration.

BACKGROUND OF THE INVENTION

Such inhalation devices are provided with a chamber for containing a pharmaceutical composition, and are configured in such a way that outside air is introduced to the chamber by the inhalation-induced pressure of a user (patient) to apply an air-generated impact to the pharmaceutical composition, thus pulverizing the pharmaceutical composition into fine particles so that the user (patient) can inhale the pulverized pharmaceutical composition into the lungs from the mouth-side flow path (disclosed in Japanese Unexamined Patent Application No. 1999-221280, for example).

Such an inhalation device disadvantageously places a burden on users (patients) who have reduced pulmonary capacity or children (patients) when generating the air impact with his/her inhalation-induced pressure.

This burden on the user can be reduced by providing an auxiliary flow path which directly reaches the mouth-side flow path of the mouthpiece, not via the chamber, so that he/she can inhale outside air which is not used for applying air impact to the pharmaceutical composition (hereinafter, referred to as auxiliary air). This auxiliary air also serves to efficiently deliver the generated fine particles to the lungs.

However, because fine particles easily coalesce/agglomerate, they tend to form coalesced or agglomerated masses due to disturbances in the air flow within the mouth-side flow path of the mouthpiece that are caused when the auxiliary air is mixed with air containing the pulverized pharmaceutical composition. Thus, some of the pulverized pharmaceutical composition does not reach the user's (patient's) lungs and adheres to his/her throat.

The pulverized pharmaceutical composition is partially dispersed in the form of agglomerated masses of fine particles when the air-generated impact applied to the pharmaceutical composition is insufficient.

In view of the above-described problems, the present invention provides an inhalation device for transpulmonary administration which can prevent agglomerated masses of fine particles of the pharmaceutical composition from entering the user's (patient's) mouth.

DISCLOSURE OF THE INVENTION

According to one aspect of the present invention, an inhalation device for transpulmonary administration comprises; a chamber for containing a pharmaceutical composition which is pulverized into fine particles by an air-generated impact for dispersal in air; an air inlet flow path for introducing to the chamber outside air to apply the air-generated impact to the pharmaceutical composition and for injecting the outside air toward the pharmaceutical composition; an inhalation flow path having a suction port located inside the chamber to inhale the pulverized pharmaceutical composition; a housing for accommodating the chamber, the air inlet flow path, and the inhalation flow path; a mouthpiece provided at one end of the housing, the mouthpiece being provided with a mouth-side flow path which communicates with the inhalation flow path, and an auxiliary flow path for directly inhaling the outside air which does not communicate with the inhalation flow path and the mouth-side flow path; wherein the inhalation device for transpulmonary administration is configured such that the air-generated impact is applied to the pharmaceutical composition by the outside air which flows into the chamber by inhalation-induced pressure generated when a user (patient) inhales air, and the pulverized pharmaceutical composition is introduced to the mouth-side flow path, and at the same time the outside air is directly introduced to the auxiliary flow path by the inhalation-induced pressure.

According to another aspect of the present invention, an inhalation device for transpulmonary administration comprises: a chamber for containing a pharmaceutical composition which is pulverized into fine particles by an air-generated impact for dispersal in air; an air inlet flow path for introducing to the chamber outside air to apply the air-generated impact to the pharmaceutical composition and for injecting the outside air toward the pharmaceutical composition; an inhalation flow path having a suction port located inside the chamber to inhale the pulverized pharmaceutical composition; a housing for accommodating the chamber, the air inlet flow path, and the inhalation flow path; a mouthpiece provided at one end of the housing, the mouthpiece being provided with a mouth-side flow path which communicates with the inhalation flow path and a divider having an orifice at least one of the mouth-side flow path or the inhalation flow path for reducing the diameter of the flow path by forming a step part; wherein the inhalation device for transpulmonary administration is configured such that the air-generated impact is applied to the pharmaceutical composition by the outside air which flows into the chamber by inhalation-induced pressure generated when a user (patient) inhales air so that the pulverized pharmaceutical composition is introduced to the inhalation flow path and the mouth-side flow path, and also passes through the orifice.

It is preferable that a plurality of dividers each having an orifice are provided at appropriately spaced intervals.

The mouthpiece has an auxiliary flow path for directly inhaling the outside air which does not communicate with the inhalation flow path and the mouth-side flow path and is preferable to have a configuration such that the pulverized pharmaceutical composition is introduced to the inhalation flow path and the mouth-side flow path, and at the same time the outside air is directly introduced to the auxiliary flow path by the inhalation-induced pressure.

According to another aspect of the present invention, an inhalation device for transpulmonary administration comprises: a chamber for containing a pharmaceutical composition which is pulverized into fine particles by air-generated impact for dispersal in air; an air inlet flow path for introducing to the chamber outside air to apply the air-generated impact to the pharmaceutical composition and for injecting the outside air toward the pharmaceutical composition; an inhalation flow path for inhaling the pulverized pharmaceutical composition; a housing for accommodating the chamber, the air inlet flow path, and the inhalation flow path; a mouthpiece provided at one end of the housing, the mouthpiece being provided with a mouth-side flow path which communicates with the inhalation flow path, and an auxiliary flow path for inhaling outside air which is not used for applying air impact to the pharmaceutical composition, and does not flow via the chamber, and furthermore allows the inhaled outside air to flow into the mouth-side flow path through an air outlet which opens into the mouth-side flow path; wherein the inhalation device for transpulmonary administration is configured such that the air outlet allows the outside air to flow in the air discharge direction of the mouth-side flow path and is formed in a ring shape along the inner circumferential wall surface of the mouth-side flow path; and the pharmaceutical composition is pulverized by the air impact generated by the outside air flowing into the chamber by inhalation-induced pressure that is generated when a user (patient) inhales air, and the pulverized pharmaceutical composition flows into the mouth-side flow path surrounded by the outside air flowing into the mouth-side flow path from the ring-shaped air outlet.

Preferably, the device is configured such that a divider has an orifice for reducing the diameter of the flow path is formed at the mouth-side flow path; and outside air containing the pulverized pharmaceutical composition passes through the orifice, and thereafter is surrounded by outside air flowing into the mouth-side flow path from the ring-shaped air outlet.

Preferably, the device is configured such that a flow-path length of the orifice is formed to be elongated to the air discharge direction of the mouth-side flow path Further, it is preferable that the device comprises the chamber for containing a non-powder cake-like form which disperses in air by an air-generated impact and accommodating a vessel sealed by a sealing member; and an unsealing member for releasing the sealed condition provided by the sealing member; wherein the inhalation device for transpulmonary administration is configured such that the vessel is unsealed by the unsealing member to establish communication between the chamber and the inside of the vessel; and the air-generated impact is applied by the inhalation-induced pressure to the pharmaceutical composition contained in the vessel.

Still further it is preferable that the device is constituted to have a check valve to prevent the pulverized pharmaceutical composition from flowing to the outside from the air inlet flow path.

According to another embodiment of the present invention, an inhalation device comprises: a main body formed cylindrically; a mouthpiece provided at one end of the main body; a vessel provided at the other end of the main body, the vessel being for containing a pharmaceutical composition which is pulverized into fine particles by an air-generated impact for dispersal in air; an inhalation flow path formed of the inner side space of the main body, the mouth piece and the vessel, the inhalation flow path being for flowing outside air containing the fine particles of the pharmaceutical composition from the vessel-side toward the mouthpiece-side; an air inlet port for introducing the outside air to the inhalation flow path; and a divider for dividing the inhalation flow path, the divider having an orifice for reducing the diameter of the inhalation flow path and being located downstream of the air inlet port; wherein the inhalation flow path has such a capacity that an air-generated impact can be applied to the pharmaceutical composition by the outside air, which is fed from the air inlet port into the inhalation flow path located upstream of the divider by an air inhalation of user.

It is preferable that the inhalation device comprises: an air outlet which opens into the inhalation flow path; and an auxiliary flow path for feeding the outside air into the inhalation flow path through the air outlet by the air inhalation of user; wherein the air outlet is provided at such a position that the outside air flowing in from the air outlet is inhaled into the mouth of the user without passing through the orifice.

BRIEF DESCRIPTION OF DRAWINGS

FIG. 3 (*b*) is an enlarged horizontal cross section of the inhalation device.

FIG. 4 (*b*) is an enlarged longitudinal cross section of the mouthpiece.

FIG. 4 (*c*) is an enlarged horizontal cross section of the mouthpiece.

FIG. 4 (*d*) is an enlarged rear view of the mouthpiece.

FIG. 11 (*b*) is an enlarged longitudinal cross section of the mouthpiece.

FIG. 11 (*c*) is an enlarged horizontal cross section of the mouthpiece.

FIG. 11 (*d*) is an enlarged rear view of the mouthpiece.

FIG. 12 (*b*) is an enlarged longitudinal cross section of the mouthpiece.

FIG. 12 (*c*) is an enlarged horizontal cross section of the mouthpiece.

FIG. 12 (*d*) is an enlarged rear view of the mouthpiece.

FIG. 17 (*b*) is a cross section showing the inhalation device.

FIG. 18 (*b*) is a cross section of the mouthpiece.

FIG. 18 (*c*) is a rear view of the mouthpiece.

FIG. 19 (*b*) is a cross section of the main body.

FIG. 19 (*c*) is a rear view of the main body.

FIG. 20 (*b*) is a cross section of the vessel having a greater depth.

BEST MODE FOR CARRYING OUT THE PRESENT INVENTION

Figure 1:
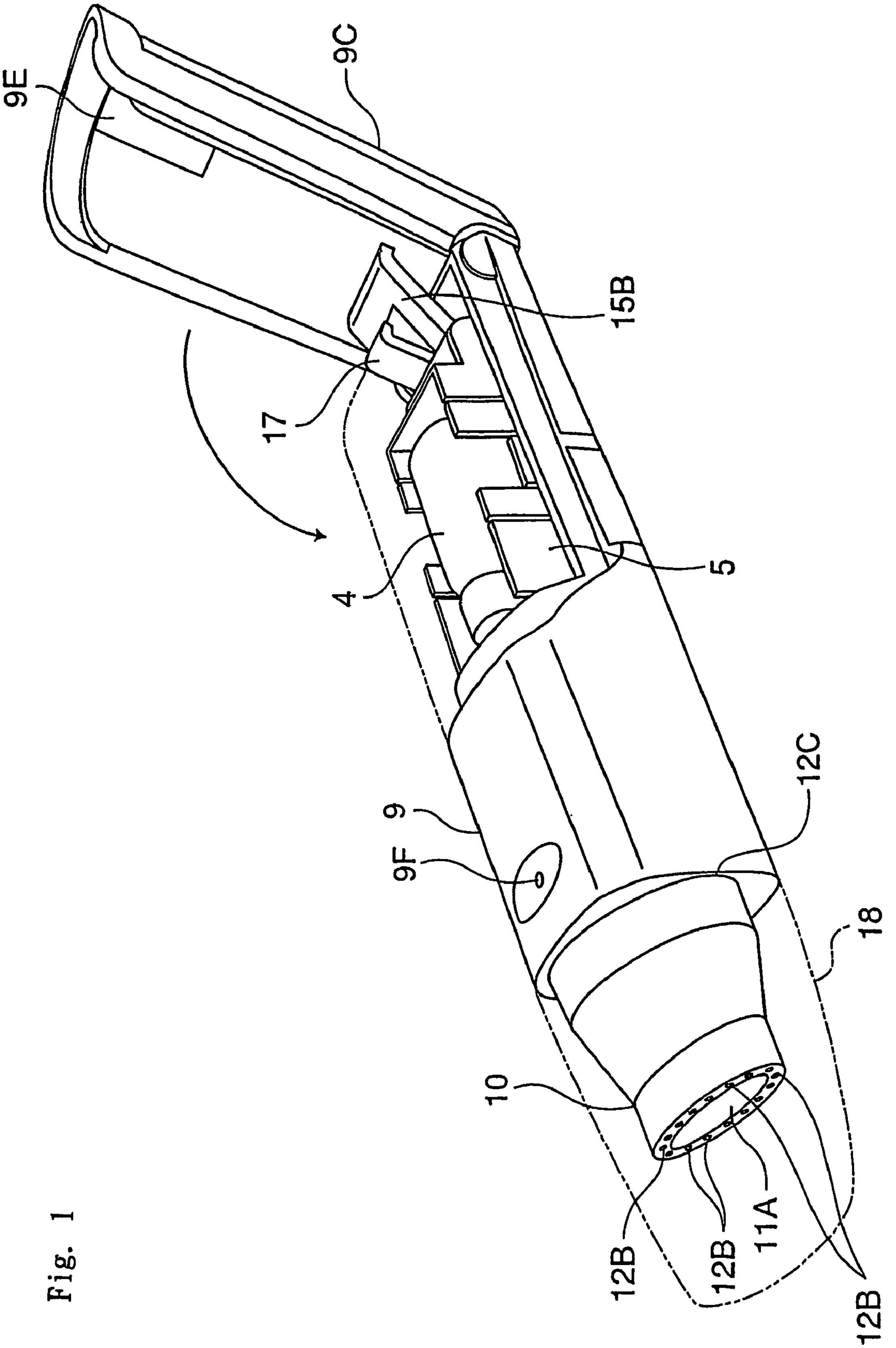
FIG. 1 is a perspective view of an inhalation device according to the first embodiment of the present invention.
Figure 2:
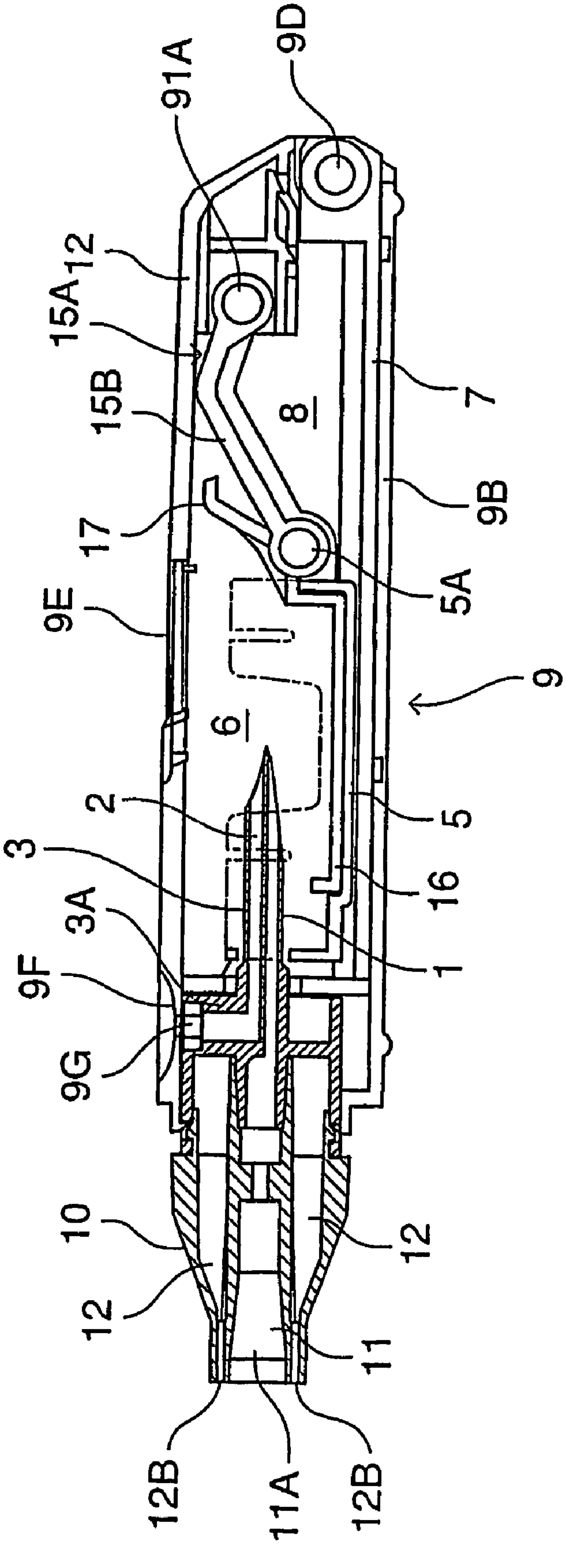
FIG. 2 is a longitudinal cross section of the inhalation device.

Hereinafter, an inhalation device of the present invention will be described according to its embodiments with reference to drawings attached hereto. FIGS. 1 through 8 show an inhalation device according to the first embodiment, FIGS. 9 through 12 show an inhalation device according to the second embodiment, and FIGS. 13 through 16 show an inhalation device according to the third embodiment.

Embodiment 1

The inhalation device in this embodiment comprises a needle part 3 (an example of an unsealing member) in which are formed an inhalation flow path 1 and an air inlet flow path 2, a holder part 5 for containing a vessel 4 which contains one dose of pharmaceutical composition A and is sealed by a stopper 4*a* (an example of a sealing member), a chamber 6 for housing the vessel 4 of the holder part 5, a guide part 7 for guiding the holder part 5 in the axial direction of the needle part 3, and a holder operating part 15 for advancing and retreating the holder part 5 along the guide part 7; these are all housed in a tubular housing 9. Moreover, a mouthpiece 10 is provided at a tip of the housing 9.

The pharmaceutical composition A can be pulverized into fine particles having a particle size suitable for transpulmonary administration by an air-generated impact that flows into the vessel. The present embodiment employs a freeze-dried composition, which will be explained in more detail later.

Figure 5:
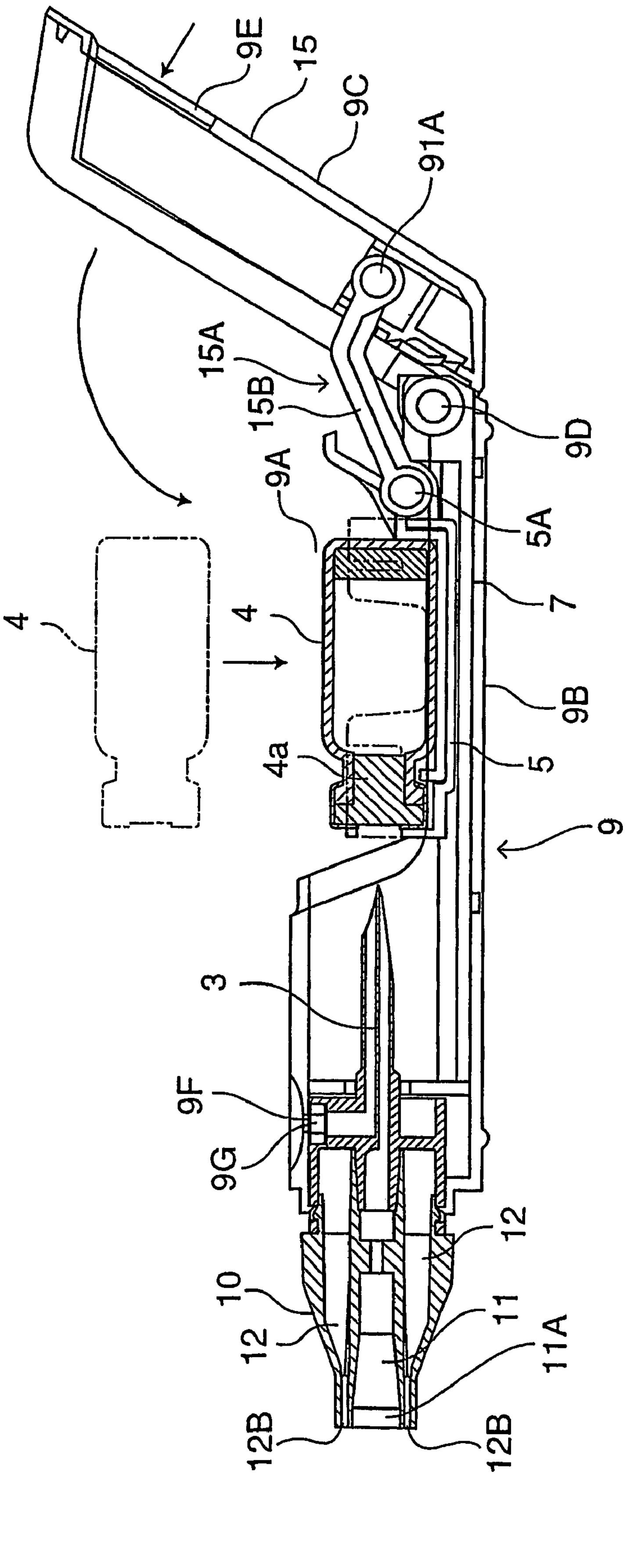
FIG. 5 is a longitudinal cross section showing the operation of the inhalation device.

As shown in FIG. 5, the housing 9 is provided with a housing main body 9B in which is formed a removal/insertion port 9A in which the holder part 5 is in a retreated position, and a lid 9C that opens and closes the removal/insertion port 9A. The lid 9C is connected to the housing main body 9B by a hinge 9D, and a window 9E for verifying whether the vessel 4 has been loaded is provided on the lid 9C.

An inlet port 9F for introducing outside air is provided on a wall of the housing 9. The inlet port 9F is equipped with a check valve 9G for preventing the pulverized pharmaceutical composition A from flowing out.

A flange-shaped partition part 3A is formed at the base end of the needle part 3, and an end of the air inlet flow path 2 of the needle part 3 opens at an outer wall surface of the partition part 3A through the inside of the partition part 3A. Moreover, a peripheral wall part 3B extends from an outer end part of the partition part 3A to the front. An engagement hole 3C is formed at the peripheral wall part 3B. An engagement projection 3D is formed at a part inserted into the front from the needle part 3, and the inhalation flow path 1 opens at the tip portion through the engagement projection 3D.

The needle part 3 is attached to the housing 9 by fitting the partition part 3A of the needle part 3 into the tip part of the housing 9. Furthermore, the axial direction of the housing 9 and the axial direction of the needle part 3 are aligned with each other.

The mouthpiece 10 is provided with a mouth-side flow path 11 and an auxiliary flow path 12. More specifically, the mouthpiece 10 consists of the mouth-side flow path 11, which communicates with the inhalation flow path 1 of the needle part 3 so as to introduce the pulverized pharmaceutical composition A, and the auxiliary flow path 12, which does not communicate with the mouth-side flow path 11 so as to introduce outside air into the user's (patient's) mouth.

Figure 3:
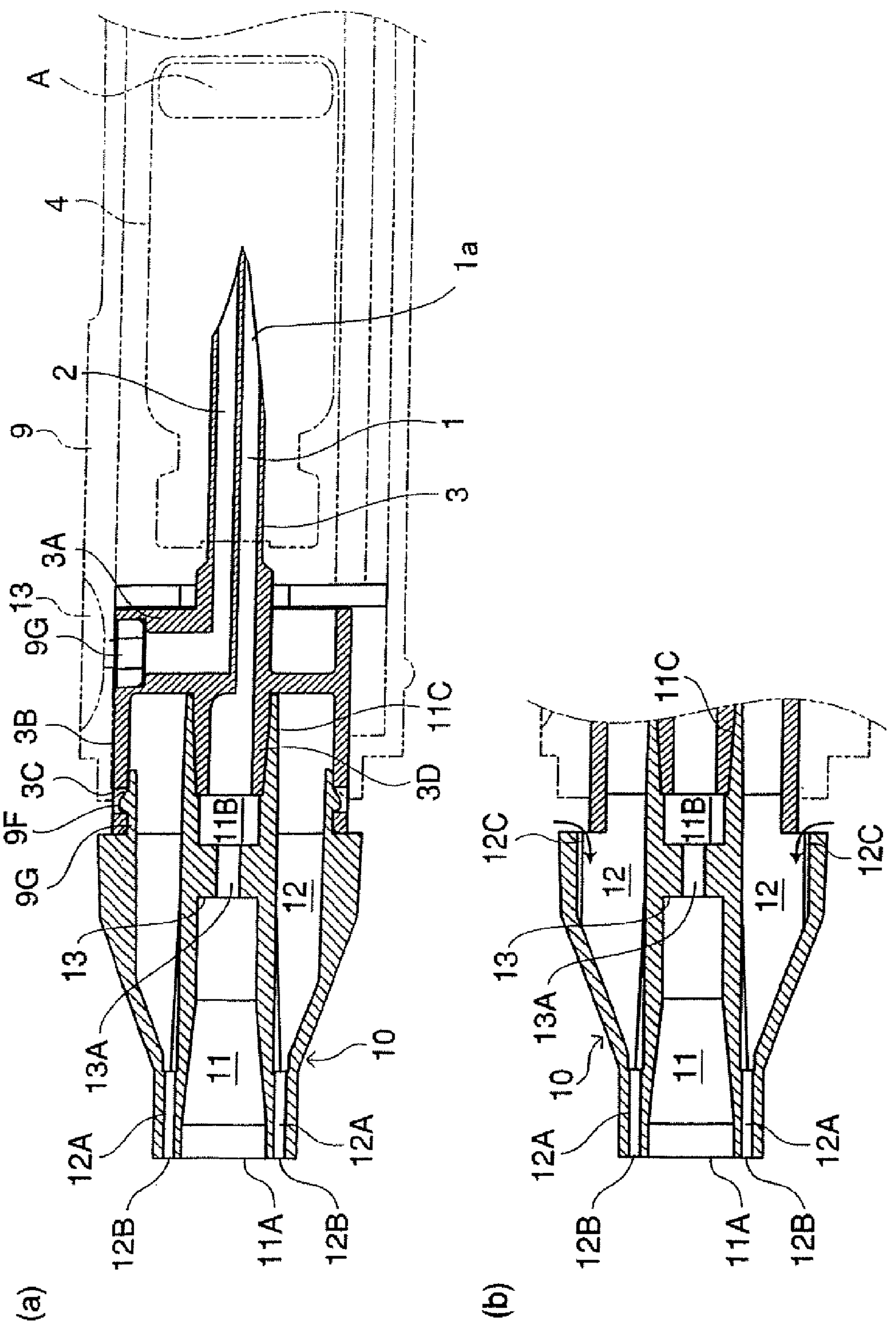
FIG. 3 (*a*) is an enlarged longitudinal cross section of the inhalation device.

The mouth-side flow path 11 passes through the mouthpiece 10. The front end and rear end of the mouth-side flow path 11 open at the front side and the rear side of the mouthpiece 10, respectively, to form a front opening 11A and a rear opening 11B. An engagement concave portion 110 is formed at the rear opening 11B. As shown in FIG. 3, a divider 13 having an orifice 13A is provided in the mouth-side flow path 11. The center of the orifice 13A is positioned at the center of the axis of the mouth-side flow path 11 of the mouthpiece 10. Suction port 1*a* is part of the inhalation flow path 1.

Figure 4:
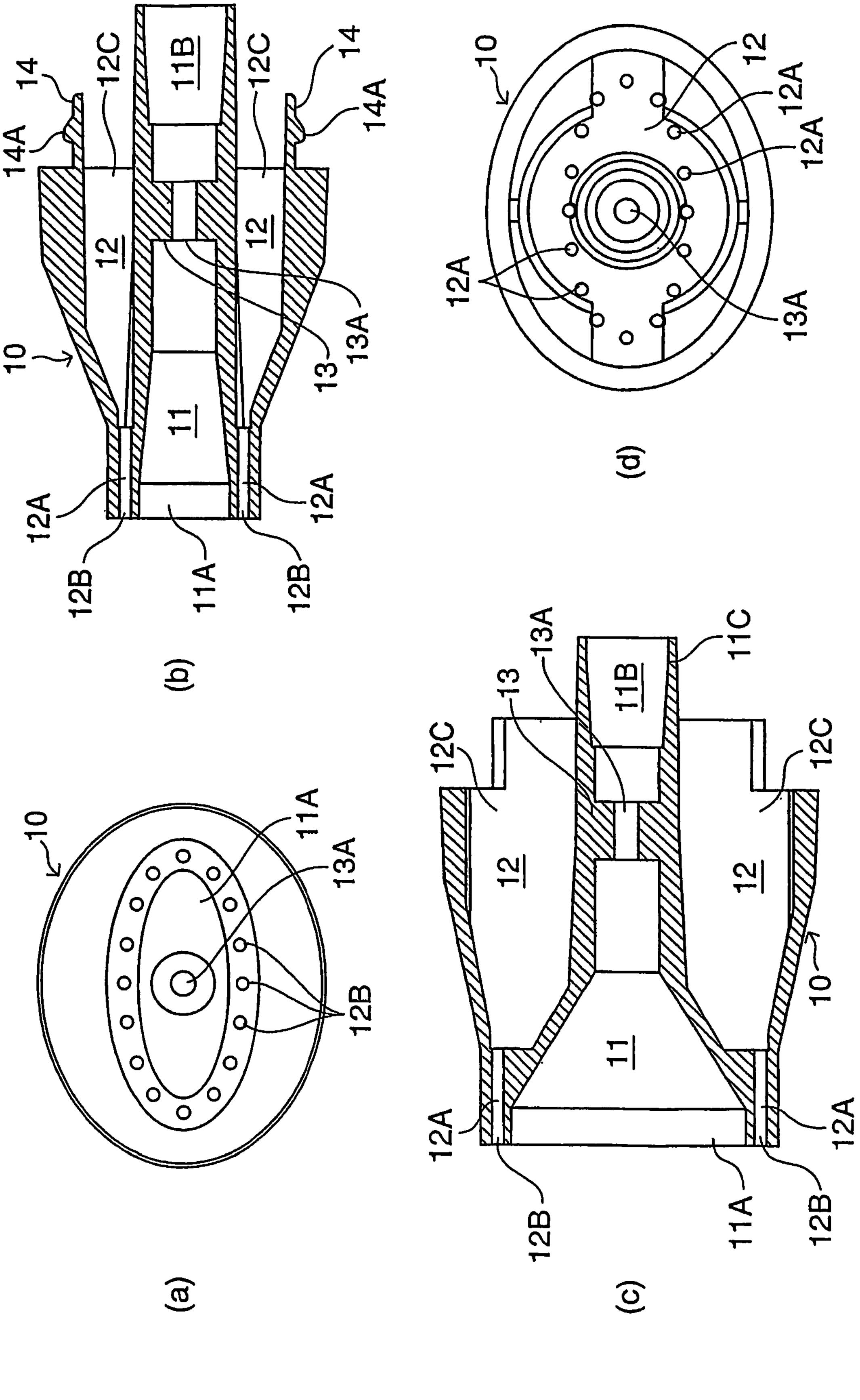
FIG. 4 (*a*) is an enlarged elevation view of the mouthpiece.

The auxiliary flow path 12 is formed annularly around the mouth-side flow path 11 as shown in FIG. 4. At the rear end of the auxiliary flow path 12 is formed an auxiliary air inlet port 12C which opens at the rear surface of the mouthpiece 10 so as to introduce outside air. The tip portion of the auxiliary flow path 12 is branched to form a plurality of inhaling branched paths 12A. These branched paths 12A open at the front surface of the mouthpiece 10 to form auxiliary openings 12B. These auxiliary openings 12B surround the front opening 11A of the mouth-side flow path 11. Thus, when a user has the mouthpiece 10 in his/her mouth, the front opening 11A of the mouth-side flow path 11 and the auxiliary openings 12B of the auxiliary flow path 12 are located in the user's mouth.

A pair of attachment portions 14 are vertically formed in the mouthpiece 10 extending toward the rear of the mouthpiece 10, and engagement projections 14A are formed in each attachment portion 14.

The engagement projection 3D of the needle part 3 is engaged with the engagement concave portion 11C of the rear opening 11B of the mouth-side flow path 11 of the mouthpiece 10 to communicate between the inhalation flow path 1 and the mouth-side flow path 11. In addition, the pair of vertically provided attachment portions 14 are fitted into the peripheral wall part 3B of the needle part 3 to engage the engagement projections 14A of the attachment portions 14 with the engagement holes 3C formed at the peripheral wall part 3B of the needle part 3, thus fixing the mouthpiece 10 to the needle part 3.

The above-described configuration prevents communication between a main flow path, which allows the user to inhale the pulverized pharmaceutical composition A into his/her mouth by the inhalation flow path 1 of the needle part 3 and the mouth-side flow path 11 of the mouthpiece 10, and a sub flow path, which allows the user to inhale auxiliary air introduced from the auxiliary air inlet port 12C by the auxiliary flow path 12. Therefore, the auxiliary air can flow directly into the user's mouth.

The holder operating part 15, which is another one of the elements constituting the inhalation device, comprises a mechanism 15A for moving the holder part 5 back and forth along the axial direction of the housing 9, and an operating lever for operating the mechanism 15A. The mechanism 15A has a connector 15B, one end of which is connected to the holder part 5 by a hinge 5A, and the other end of which is connected to the lid 9C by a hinge 91A. The lid 9C also serves as the above-mentioned operating lever. By opening and closing the lid 9C, the holder part 5 is advanced and retreated along the guide part 7. The holder part 5 is provided with a remover 16 for lifting the vessel 4 from the base thereof to remove the vessel 4, and a lever 17 for lifting the vessel 4 is formed on the remover 16.

Figure 6:
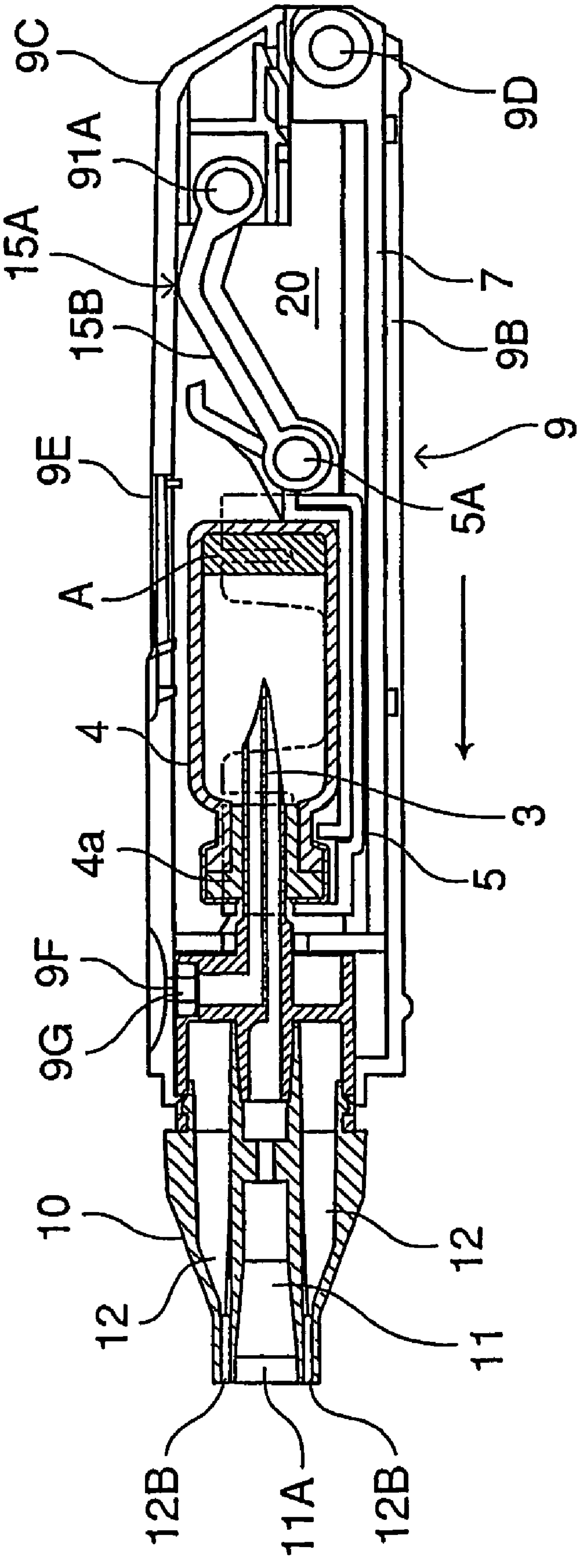
FIG. 6 is a longitudinal cross section showing the operation of the inhalation device.

The inhalation device is used as follows. Firstly, the lid 9C is lifted to open the removal/insertion port 9A of the housing 9 as shown in FIG. 5, whereby the holder part 5 is pulled backward to reach the removal/insertion port 9A of the housing 9. Next, the vessel 4 is attached to the holder part 5 with the stopper 4*a* facing forward. Next, the lid 9C is pushed down to close the removal/insertion port 9A of the housing 9 as shown in FIG. 6, whereby the holder part 5 is pushed toward the needle part 3 by the connector 15B, and the stopper 4*a* of the vessel 4 is pierced by the tip of the needle part 3, thus placing the inhalation flow path 1 and the air inlet flow path 2 of the needle part 3 in communication with the inside of the vessel 4.

Subsequently, the user takes the mouthpiece 10 in his/her mouth and inhales air from the vessel 4 through both the mouth-side flow path 11 of the mouthpiece 10 via the inhalation flow path 1 of the needle part 3 by the user's (patient's) inhalation-induced pressure. During this process, the inside of the vessel 4 becomes subject to negative pressure and thus the check valve 9G opens, and outside air flows into the vessel 4 through the air inlet flow path 2 of the needle part 3. As a result, an air-generated impact is created in the vessel 4, the pharmaceutical composition A is pulverized into fine particles, and the fine particles are delivered into the user's (patient's) lungs from the inhalation flow path 1 and the mouth-side flow path 11. At the same time, the auxiliary air is directly inhaled into the user's (patient's) mouth from the auxiliary air inlet port via the auxiliary flow path 12. As described above, the auxiliary air is not mixed with air containing the pulverized pharmaceutical composition A flowing through the inhalation flow path 1 and the mouth-side flow path 11, which prevents the coalescence/agglomeration of fine particles due to the flow of the auxiliary air. By allowing inhalation of the auxiliary air, the inhalation device can thus reduce the burdens on a user (patient) having reduced pulmonary capacity or the burden on a child (patient).

Even if the pharmaceutical composition A were to be partially dispersed in the form of agglomerated masses because a user's (patient's) inhalation strength is weak, the agglomerated masses would be crushed against the divider 13 located at the periphery of the orifice 13A in the mouth-side flow path 11 of the mouthpiece 10 and thus dispersed and pulverized into fine particles when the agglomerated masses pass through the orifice 13A. The agglomerated masses formed when passing through the mouth-side flow path 11 are also dispersed through the divider 13.

The check valve 9G prevents the pulverized pharmaceutical composition A from flowing to the outside from the inlet port even when the user (patient) erroneously blows air into the vessel 4 from the mouth-side flow path 11 of the mouth piece 10.

Figure 7:
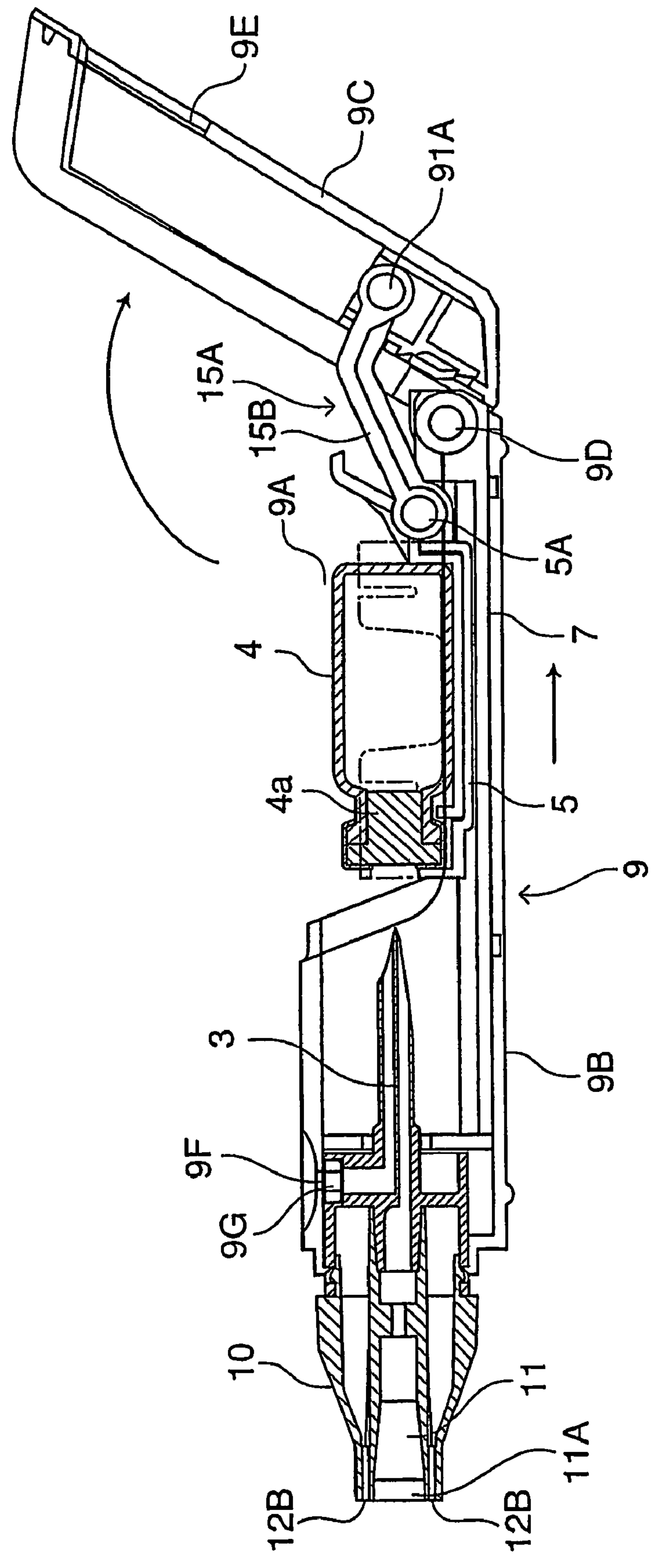
FIG. 7 is a longitudinal cross section showing the operation of the inhalation device.
Figure 8:
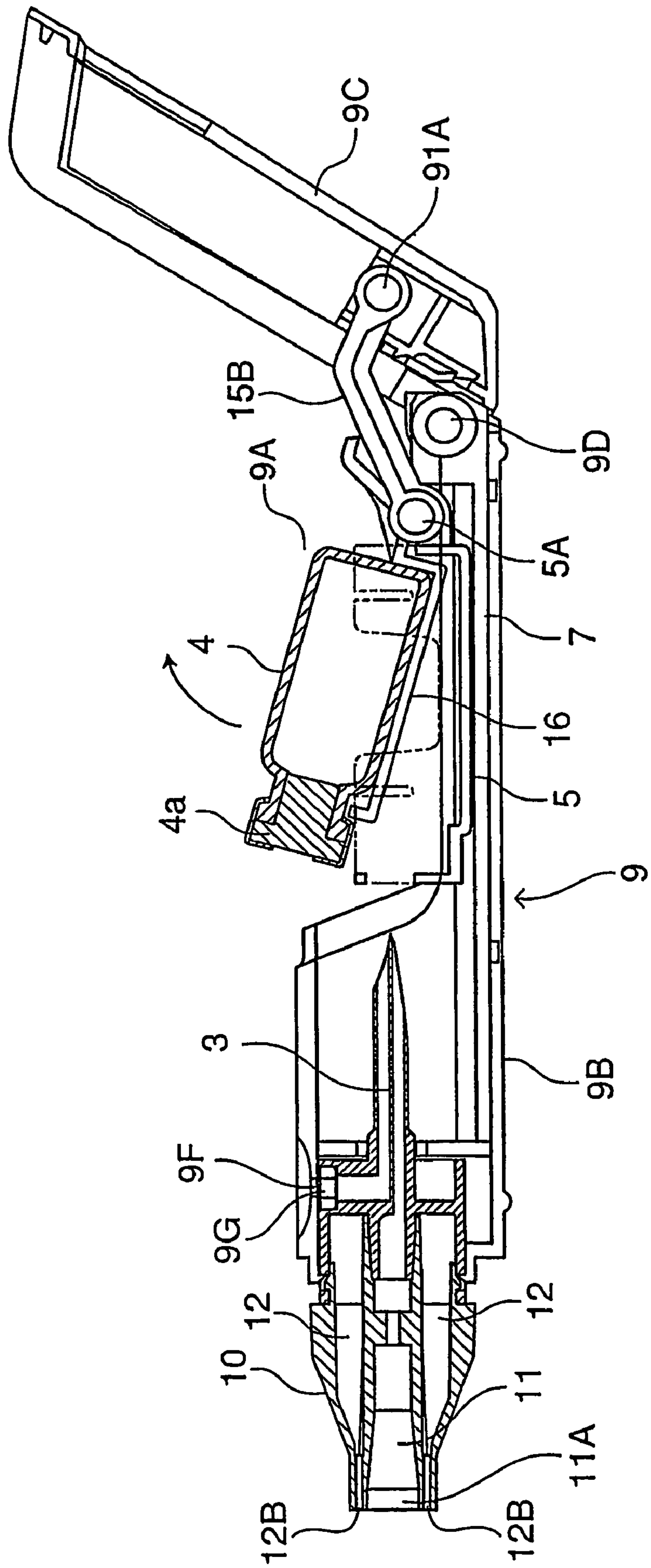
FIG. 8 is a longitudinal cross section showing the operation of the inhalation device.

After transpulmonary administration is completed, the lid 9C is lifted to pull the holder part 5 back up to the removal/insertion port 9A of the housing 9 as shown in FIG. 7, and then the remover 16 is lifted by the lever 17 and the vessel 4 is removed from the holder part 5 as shown in FIG. 8.

When the inhalation device is not being used, the mouthpiece 10 is closed with a cap 18 as shown in FIG. 1.

As described above, the air flow rate of one inhalation by the user (patient) is generally in the range of 5 to 300 L/min. Considering the possible respiratory ability of the user (patient), the inhalation device of the present invention is set so that the volume of the vessel 4 is about 5 ml, the bore (diameter) of the air inlet flow path 2 is about 2 mm, the bore (diameter) of the inhalation flow path 1 is about 2 mm, and the bore (diameter) of the inhaling branched path is about 1 mm.

EMBODIMENT 2

Figure 9:
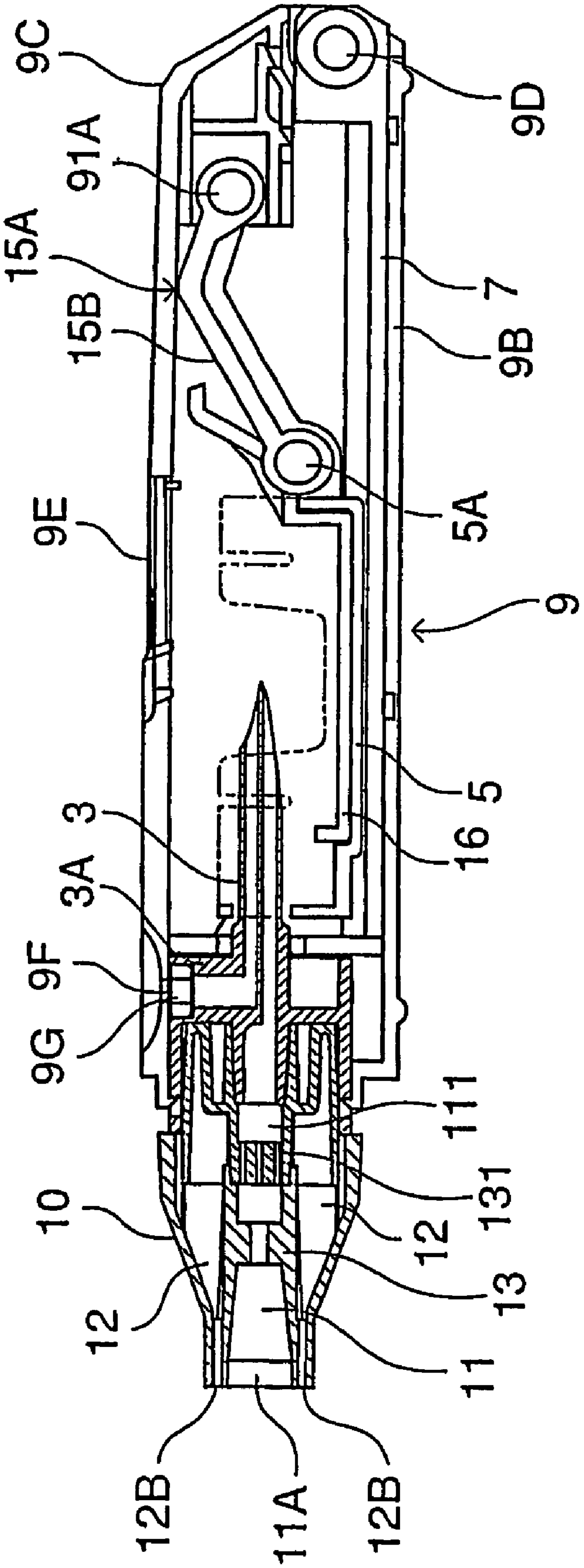
FIG. 9 is a perspective view of an inhalation device according to the second embodiment of the present invention.
Figure 10:
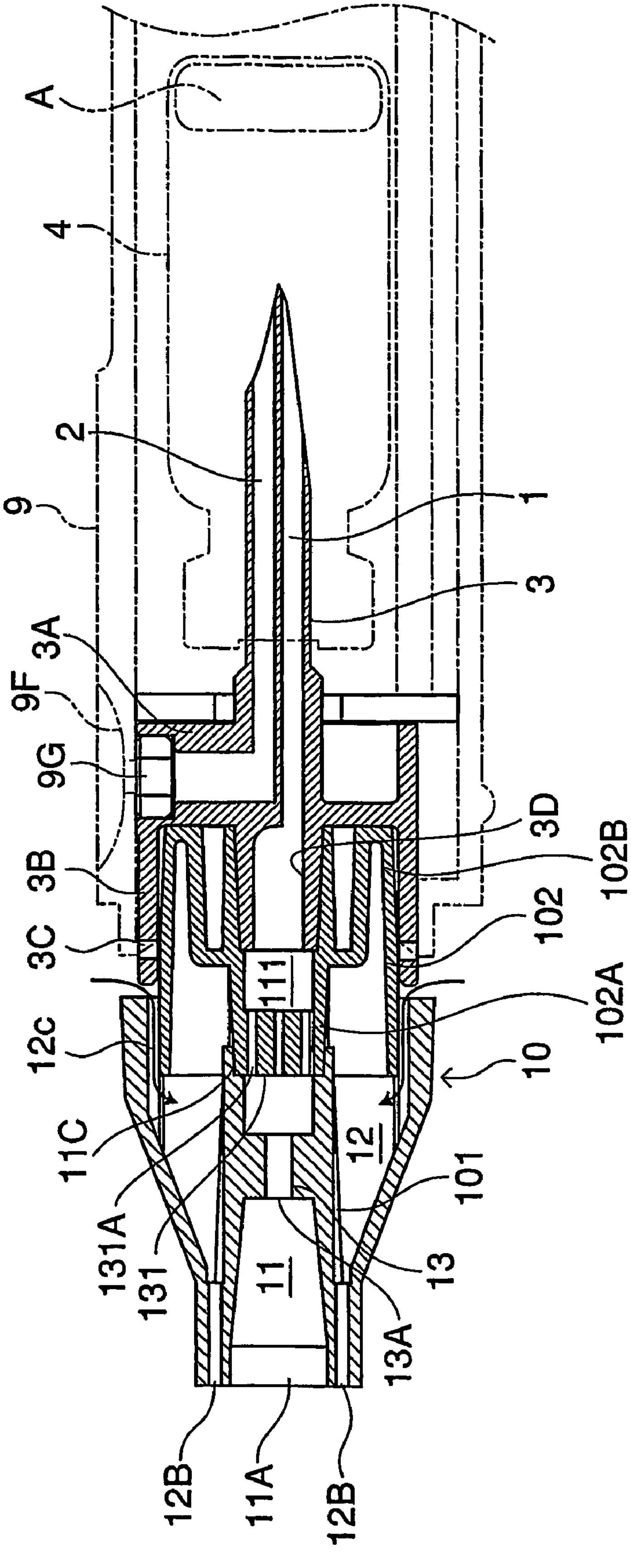
FIG. 10 is a longitudinal cross section of the inhalation device.

An inhalation device of the present embodiment is provided with two dividers 13 and 131 that are formed along the mouth-side flow paths 11 and 111 of the mouthpiece 10 at appropriately spaced intervals as shown in FIGS. 9 and 10. The components constituting the device other than the mouthpiece 10 are the same or similar to those of the first embodiment, and thus the same or similar components are designated by the same numerals as in the first embodiment, and their detailed descriptions are omitted here.

Figure 11:
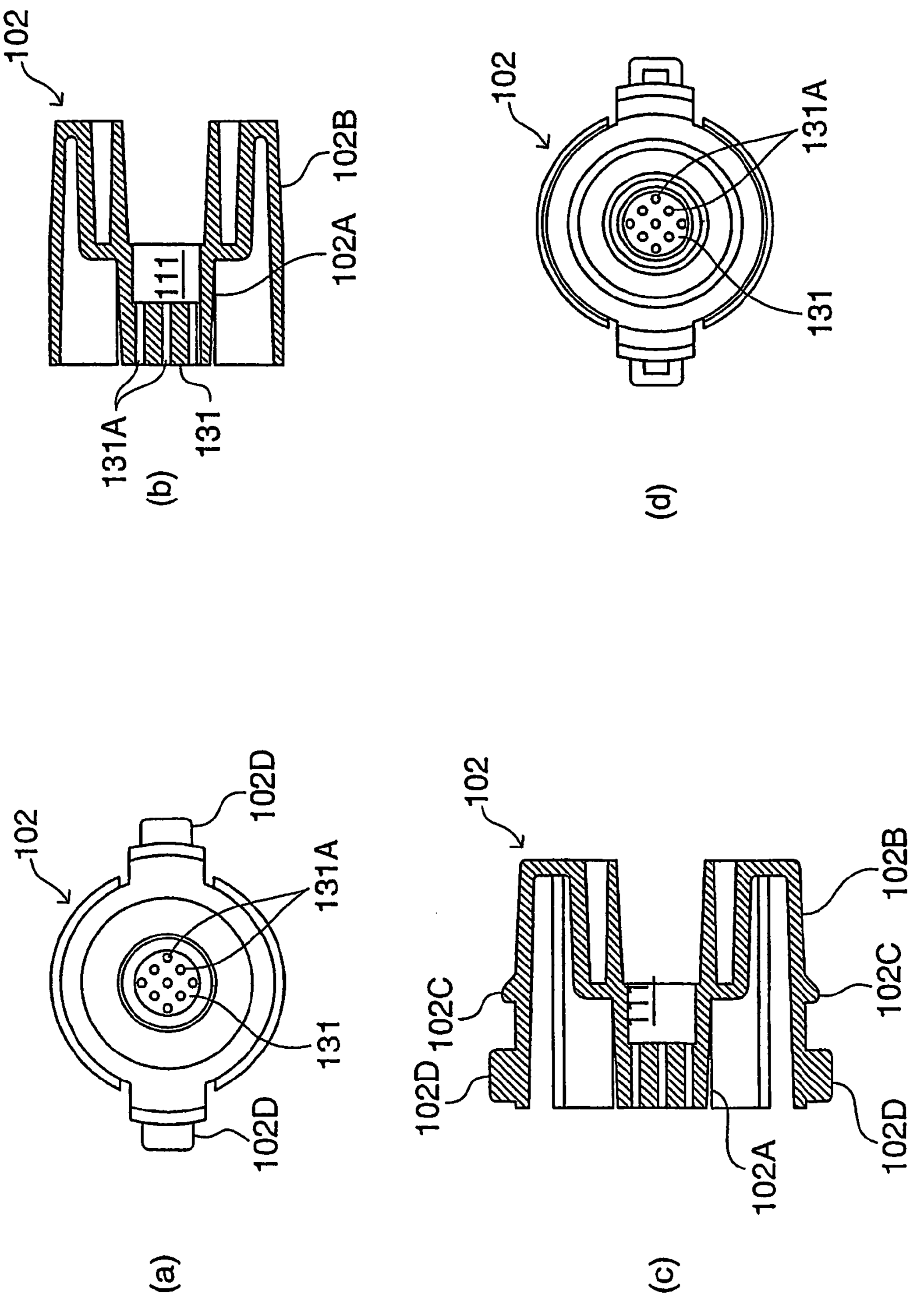
FIG. 11 (*a*) is an enlarged elevation view of the rear divided body that forms part of the mouthpiece of the inhalation device.

A single orifice 13A, the center of which is positioned at the center of the axis of the mouth-side flow path 11 of the mouthpiece 10, is formed at the divider 13 in the front part of the mouthpiece. A plurality of orifices 13A are provided at substantially equally spaced intervals at the divider 131 in the rear part of the mouthpiece, as shown in FIG. 11.

The mouthpiece 10 is comprised of two separable parts: a front part and a rear part. The divider 13 is formed in a front divided body 101 while the divider 131 is formed in a rear divided body 102.

Figure 12:
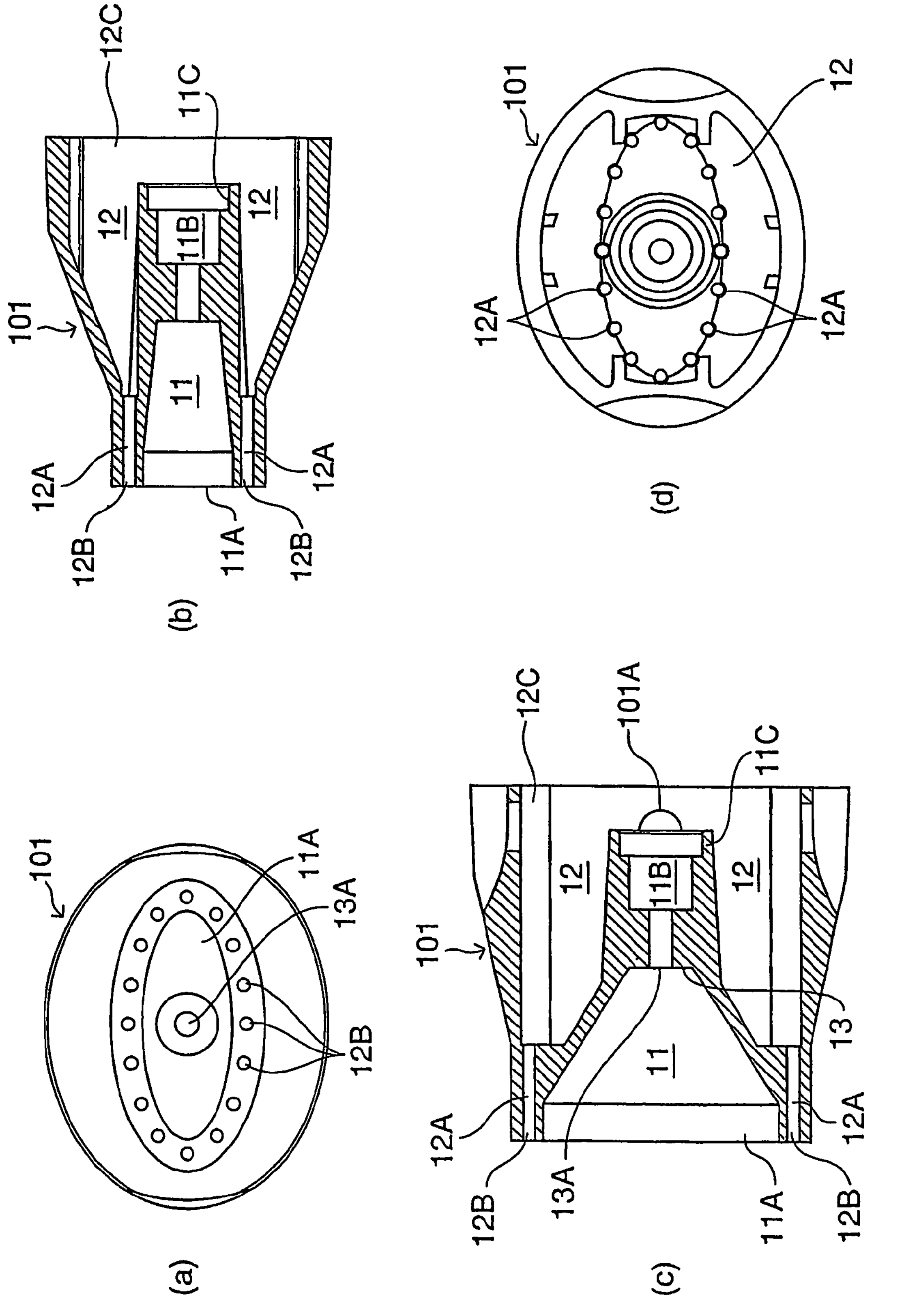
FIG. 12 (*a*) is an enlarged elevation view of the front divided body that forms part of the mouthpiece.

As shown in FIG. 12, the front divided body 101 is provided with a mouth-side flow path 11 and an auxiliary flow path 12 as in the mouthpiece 10 of the first embodiment. An engagement concave portion 11C is formed at a rear opening 11B of the mouth-side flow path 11. An engagement concave portion 101A is formed at an inner wall of the auxiliary flow path 12. As shown in FIG. 11, the rear divided body 102 is configured by integrating an internal tube 102A containing the mouth-side flow path 111 and an external tube 102B. The external tube 102B is provided with engagement projections 102C and 102D.

The tip of the internal tube 102A of the rear divided body 102 is fitted to the engagement concave portion 101C of the front divided body 101 and the engagement projection 102D of the external tube 102B is engaged with the engagement concave portion 101A of the front divided body 101. This establishes connection between the front and rear divided bodies 101 and 102. The external tube 102B of the rear divided body 102 is engaged with the peripheral wall part 3B of the needle part 3, the engagement projection 102C of the external tube 102B is engaged with the engagement hole 3C of the peripheral wall part 3B, and the internal tube 102A is engaged with the engagement projection 3D of the needle part 3. The mouthpiece 10 is thus positioned at the tip of the housing 1.

The inhalation device of the present embodiment is used in the same manner as described above. The auxiliary air is introduced from the auxiliary air inlet port 12C of the front divided body 101 of the mouthpiece 10 as shown by an arrow in FIG. 10.

The dividers 13 and 131 are provided at two locations in the mouth-side flow path 11 of the mouthpiece 10, thus allowing them to expedite the dispersal of agglomerated masses of fine particles of the pharmaceutical composition. Dividers may also be provided at three or more locations.

EMBODIMENT 3

Figure 13:
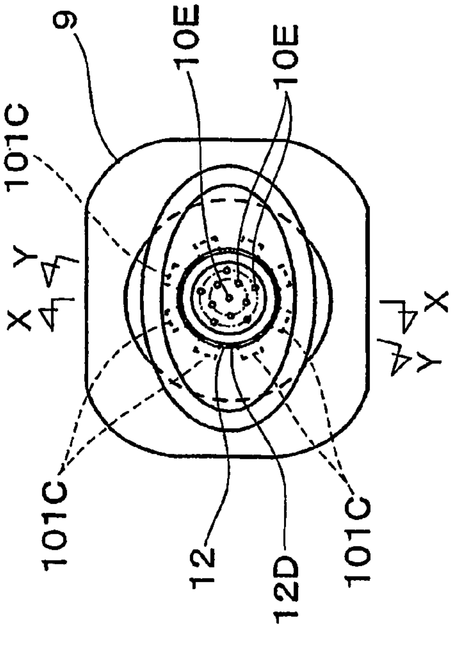
FIG. 13 is an elevation view showing an inhalation device according to the third embodiment of the present invention.
Figure 14:
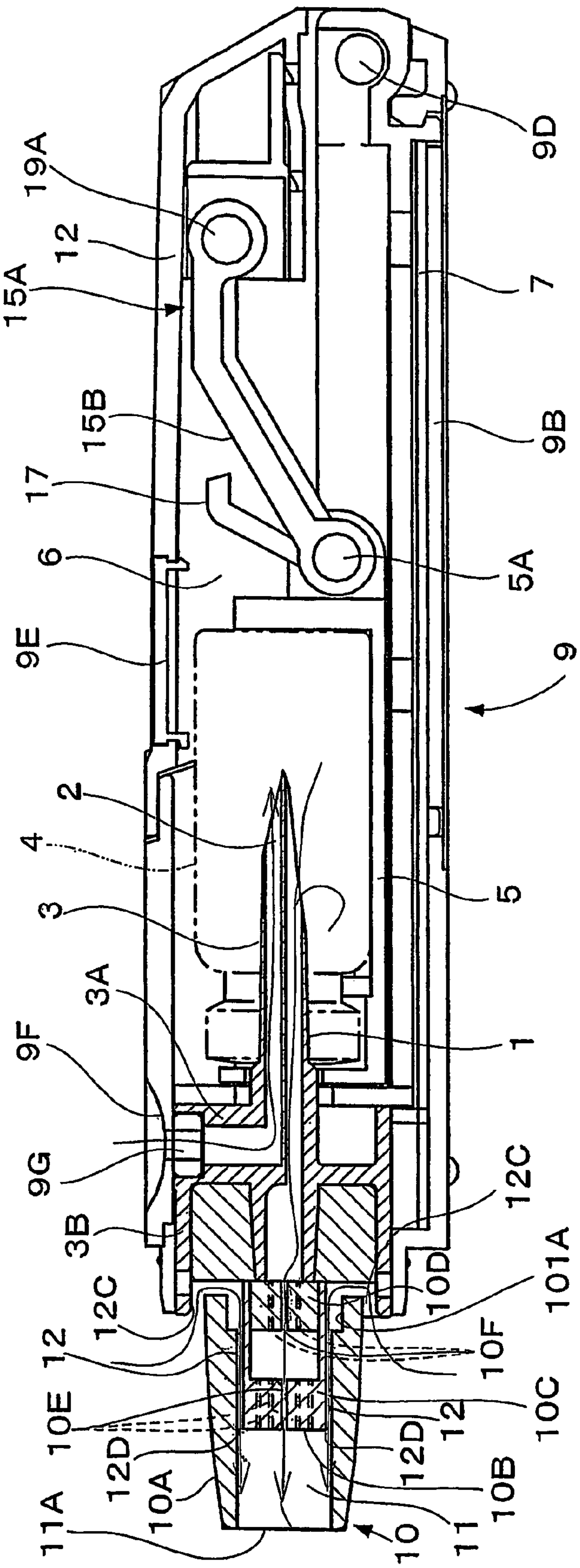
FIG. 14 is a cross section taken on line X-X of FIG. 13.
Figure 15:
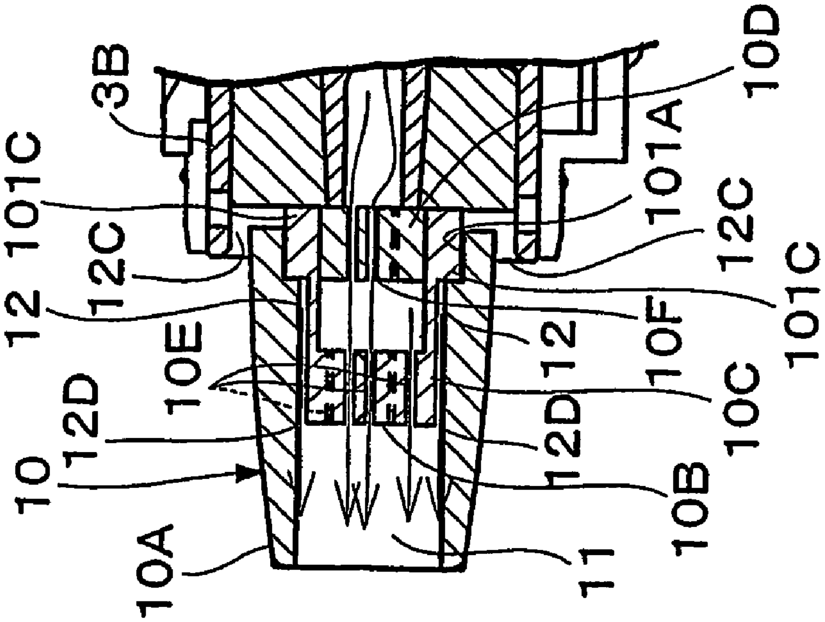
FIG. 15 is a cross section taken on line Y-Y of FIG. 13.

As shown in FIGS. 13 through 15, the mouthpiece 10 is provided with an outer shell 10A, a tubular internal member 10C having a divider 10B, and a dividing block 10D. The composition of the inhalation device other than the mouthpiece 10 is the same as in the first embodiment, and their detailed descriptions are omitted here.

The mouthpiece 10 is assembled by fitting the internal member 10C into the outer shell 10A from the rear, and fitting the dividing block 10D into the internal member 10C from the rear. A plurality of spacers 101C project along an outer circumferential surface of the internal member 10C of the rear side at predetermined spaced intervals in the circumferential direction. A step part 101A is formed at an inner circumferential surface of the outer shell 10A throughout its length in the circumferential direction. The spacers 101C are fitted into the step part 101A of the outer shell 10A, and thus a cylindrical space is formed between the outer shell 10A and the internal member 10C, to be served as an auxiliary flow path 12.

A ring-shaped air outlet 12D is formed at a tip part of the auxiliary flow path 12. The air outlet 12D is located in the midway of the mouth-side flow path 11 and allows the outside air to flow in the air discharge direction of the mouth-side flow path 11. The auxiliary air introduced from the auxiliary air inlet port 12C flows into the auxiliary flow path 12 through the spaces formed between the spacers 101C, and flows into the mouth-side flow path 11 in a ring form from the air outlet 12D through the auxiliary flow path 12.

The divider 10B and the dividing block 10D of the internal member 10C are provided with a plurality of orifices 10E and 10F, respectively which are provided at substantially uniformly spaced intervals. The dividers 10B and the dividing block 10D of the internal member 10C are enlarged in thickness, which elongates the orifices 10E and 10F to the air discharge direction. The orifices 10E and 10F are not to be located forward of the air outlet 12D.

The inhalation device of the present embodiment is used as follows. The inhalation flow path 1 and the air inlet flow path 2 of the needle part 3 are communicated with the inside of the vessel 4 as described in the above. A user (patient) takes the mouthpiece 10 in his/her mouth for inhalation, and thus the auxiliary air flows into the auxiliary flow path 12 from the auxiliary air inlet 12C, and then flows out in a laminar flow from the air outlet 12D into the mouth-side flow path 11. The pharmaceutical composition is pulverized into fine particles by air impact generated by outside air flowing from the air inlet flow path 2 of the needle part 3. The outside air containing fine particles of the pharmaceutical composition flows into the mouth-side flow path 11 from the inhalation flow path 1, and passes through the orifices 10E, and thereafter flows out from the front opening 11A of the mouthpiece 10 with surrounded by the auxiliary air flowing out from the air outlet 12D. Thus, the outside air containing fine particles of the pharmaceutical composition is prevented from disturbing, which can suppress dispersal of fine particles of the pharmaceutical composition.

The mouthpiece 10 is set so that the auxiliary air flows into the mouth-side flow path 11 from the air outlet 12D before the outside air containing fine particles pass through the orifices 10E. Thus, the outside air containing fine particles are surely surrounded by the auxiliary air in a laminar flow.

The auxiliary air avoids the outside air containing fine particles from contacting inner circumferential wall surface of the mouth-side flow path 11, which prevents the fine particles of the pharmaceutical composition from adhering to the wall surface of the mouth-side flow path 11 or the like even if the mouthpiece 10 is formed of a material such as a plastic which is likely to have static electricity.

Figure 16:
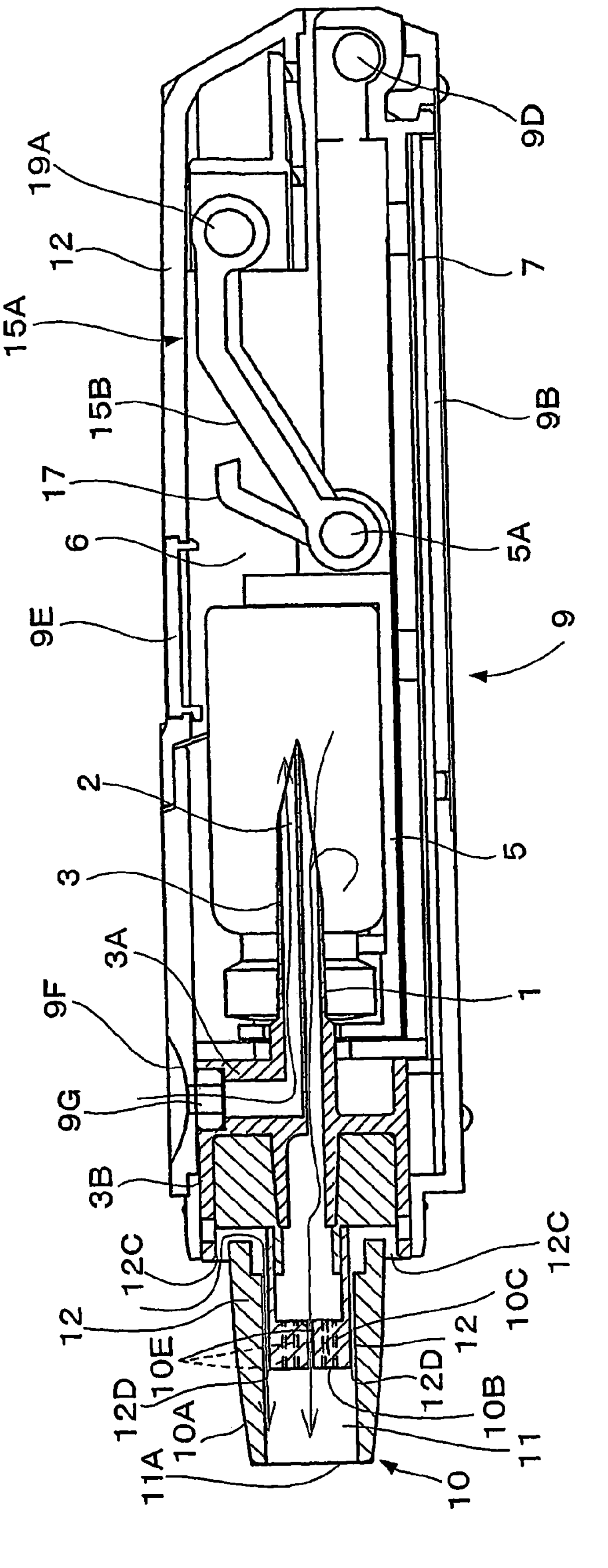
FIG. 16 is a cross section showing an inhalation device having an orifice formed at the front side only of the mouthpiece.

FIG. 16 shows an inhalation device having a plurality of orifices 10E formed at the front side only of the mouthpiece 10.

EMBODIMENT 4

As shown in FIGS. 17 through 20, the inhalation device is provided with a main body 100*a*, a mouthpiece 100*b* and a vessel 100*c* for containing pharmaceutical composition A which is pulverized into fine particles by an air-generated impact for dispersal in air.

Figure 18:
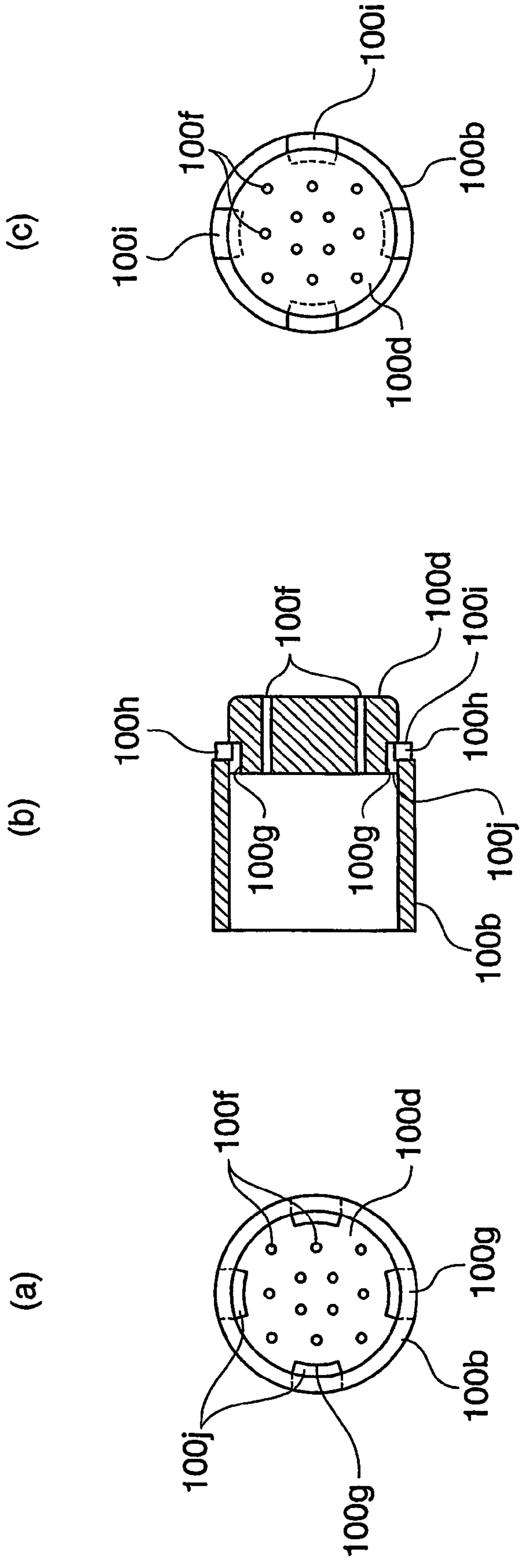
FIG. 18 (*a*) is an elevation view of the mouthpiece.

As shown in FIG. 18, the mouthpiece 100*b* is formed cylindrically, and a dividing part 100*e* inside the mouthpiece 100*b* is formed by a dividing member 100*d*. A plurality of orifice 100*f* is provided on the disc-shaped dividing member 100*d*, and notches 100*g* are formed at the outer circumferential surface of the dividing member 100*d*. Due to the notch 100*g*, an auxiliary flow path 100*h* for inhaling an auxiliary air into the mouthpiece 100*b* is formed between the mouthpiece 100*b* and the dividing member 100*d*. An air inlet port 100*i* is provided at one end of the auxiliary flow path 100 and an air outlet 100*j* at the other end of the auxiliary flow path 100*h*. As described in the above Embodiment 3, the air outlet 100*j* may be formed into a ring shape.

Figure 19:
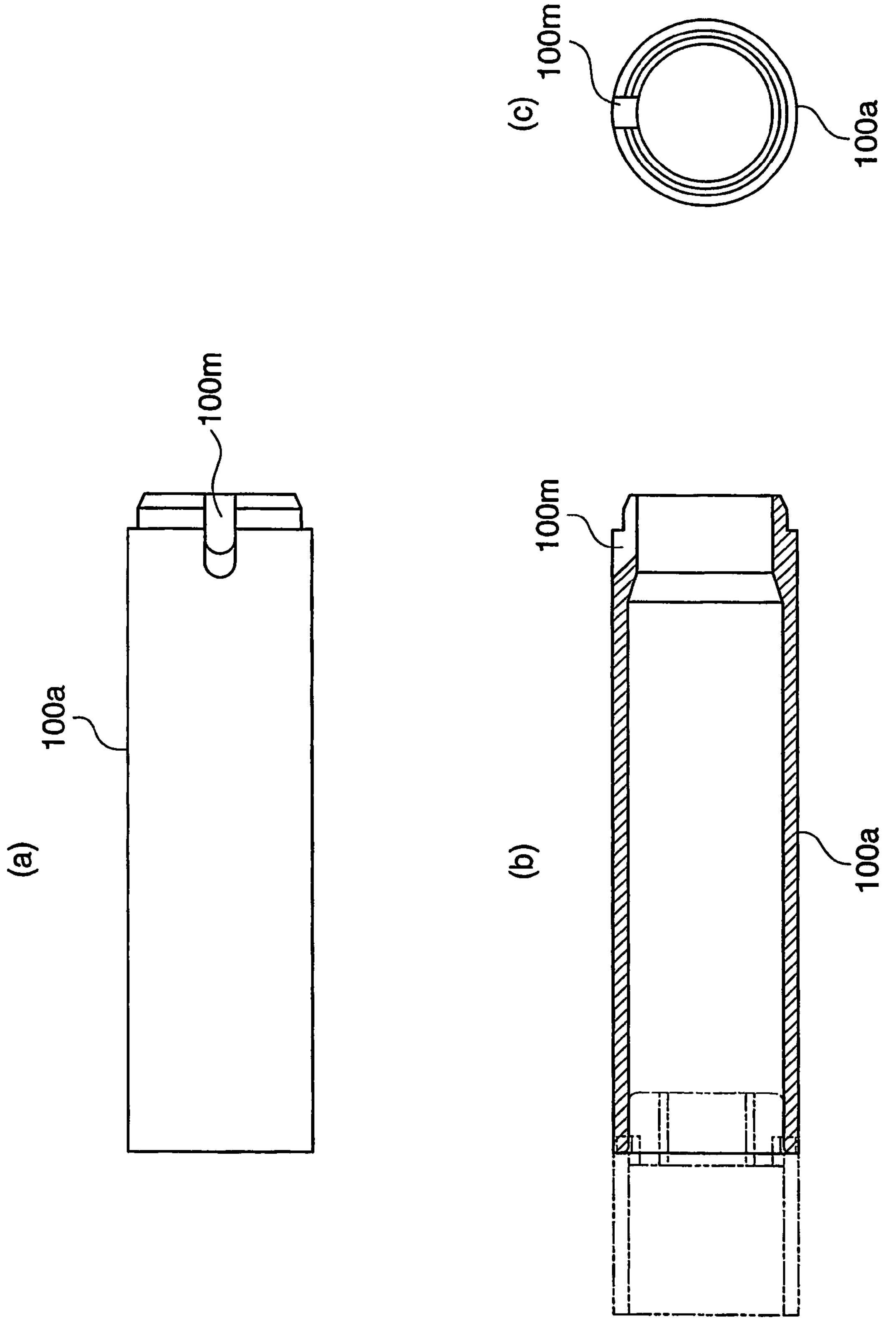
FIG. 19 (*a*) is a plan view of a part of the main body.

As shown in FIG. 19, the main body 100*a* is formed cylindrically, and a notch 100*m* for forming an air inlet port 100*k* is provided at the end of the main body 100*a*.

Figure 20:
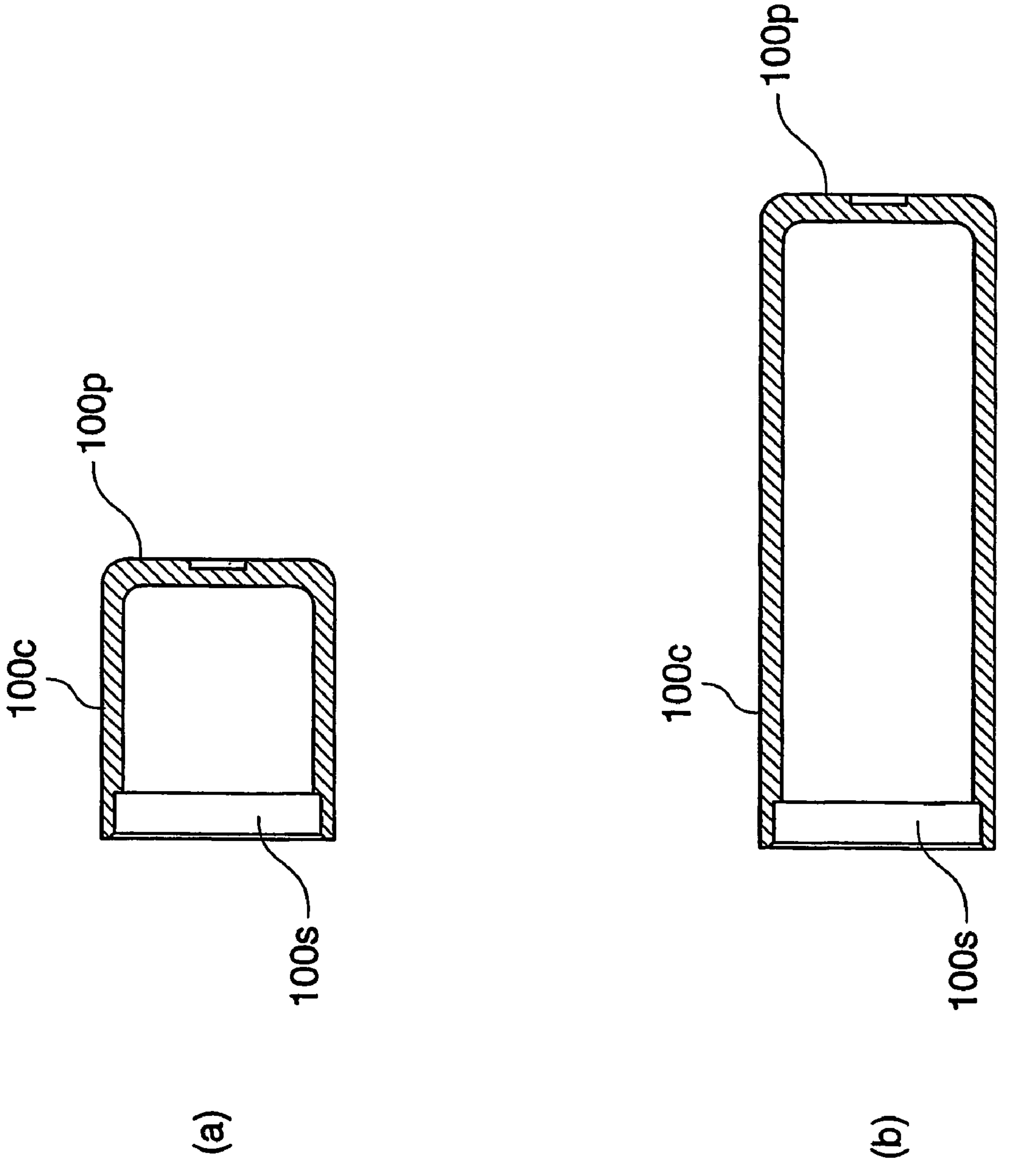
FIG. 20 (*a*) is a cross section of the vessel.

As shown in FIG. 20, the vessel 100*c* is formed cylindrically and has a bottom part 100*p*.

The inhalation device is assembled by attaching the mouthpiece 100*b* to one end of the main body 100*a* and by detachably attaching the vessel 100*c* to the other end of the main body 100*a*. As shown in FIGS. 20(*a*) and 20(*b*), the depth of the vessel 100*c* may be changed as appropriate.

Figure 17:
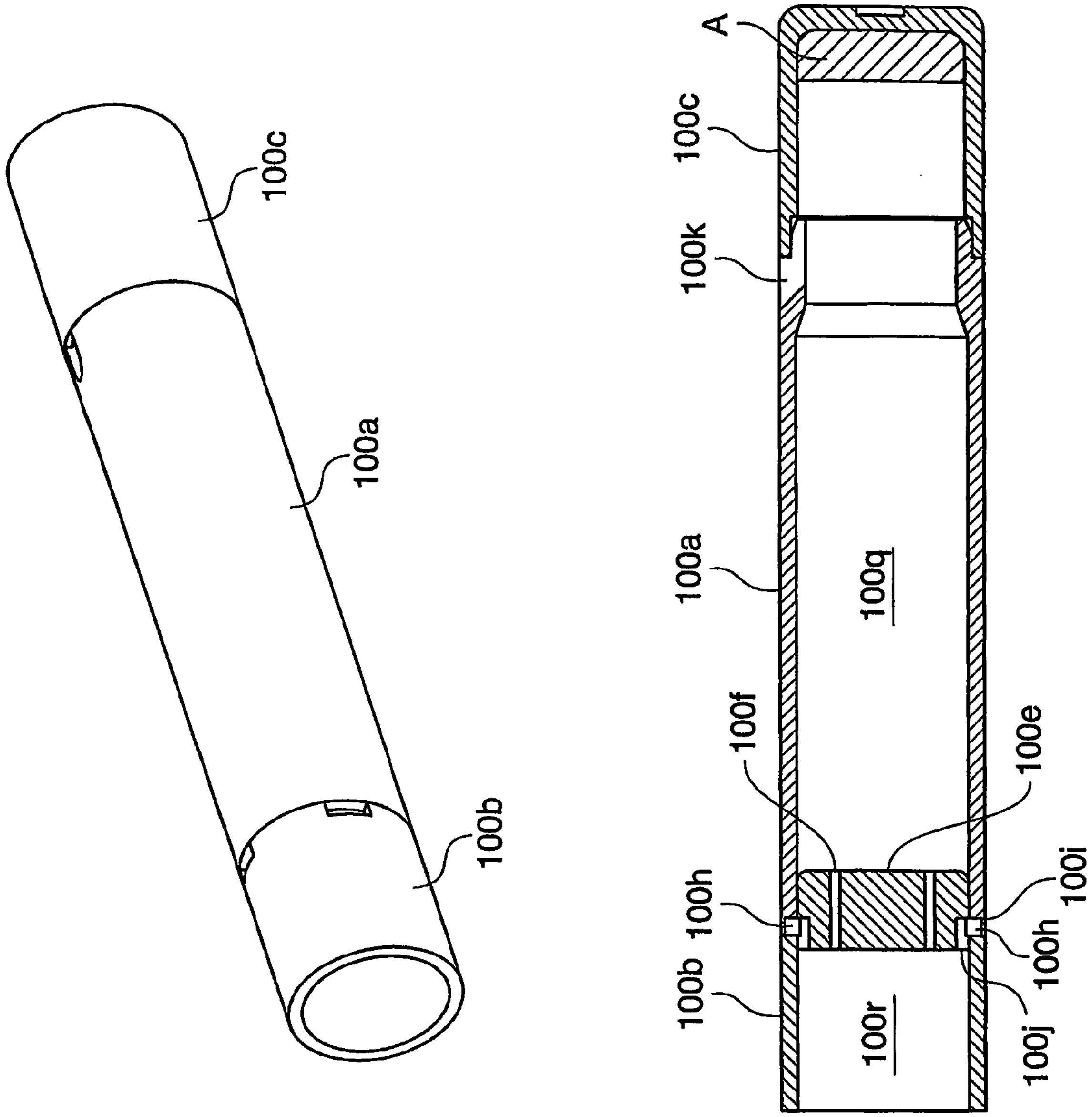
FIG. 17 (*a*) is a perspective view of an inhalation device according to the fourth embodiment of the present invention.

As shown in FIG. 17, the inhalation device is provided with an inhalation flow path 100*q* and a mouthpiece-side inhalation flow path 100*r* for inhaling the outside air containing fine particles of the pharmaceutical composition A, which are formed of the inner side space of the main body 100*a*, the mouthpiece 100*b* and the vessel 100*c*. The inhalation flow path 100*q* includes the inside space of the vessel 100*c*.

The capacity of the inhalation flow path 100*q* and the inhalation flow path 100*r* taken altogether is in such an amount that the inhalation flow path 100*q* located upstream of the divider 100*e* is filled with the outside air which is allowed to flow from the air inlet port 100*k* by the inhaled air of a patient so that the air-generated impact can be applied to the pharmaceutical composition A. An example of the capacity is 3 to 100 ml. If necessary, the inhalation device can be downsized to almost the same size as, or smaller than, a cigarette. For example, the inhalation device may have a total length of 80 mm, an outside diameter of 10 mm, and an inside diameter of 8 mm.

The inhalation device of the present embodiment can be constituted only by joining the main body 100*a* in cylinder form, the mouthpiece 100*b* and the vessel 100*c* of the pharmaceutical composition A, and providing the air inlet port 100*k* of the outside air and the dividing part 100*e* having the orifice 100*f*. Thus the inhalation device can be downsized to almost the same size as, or smaller than, a cigarette, and become less prone to being out of order due to its simple structure.

The pharmaceutical composition A is sealed in the vessel 100*c* by filing up an opening 100*s* of the vessel 100*c* with a sealant. At the use of the inhalation device, the vessel 100*c* is attached to the main body 100*a* after removing the sealant. The sealant may be made of aluminium, plastic and the like.

The inhalation device provided with the vessel 100*c* may be stored in a moisture-proof case or a moisture-proof bag and may be taken out therefrom at the time of use. A sealant is necessary in this case.

The inhalation device according to the invention is used as follows. The inhalation flow path 100*q* is filled with the outside air due to an air inhalation of patient, so that the pharmaceutical composition A can be pulverized by the air impact. The outside air containing the fine particles of the pharmaceutical composition A is inhaled into the user's mouth after passing through the orifice 100*f* and then the inhalation path 100r inside the mouthpiece 100b. Agglomerated masses of the pharmaceutical composition A can be dispersed by passing through the orifice 100f. Due to the inhaled air of patient, the auxiliary air flows into the mouthpiece 100b from the auxiliary flow path 100h, thereby reducing the burden on the patient.

Figure 21:
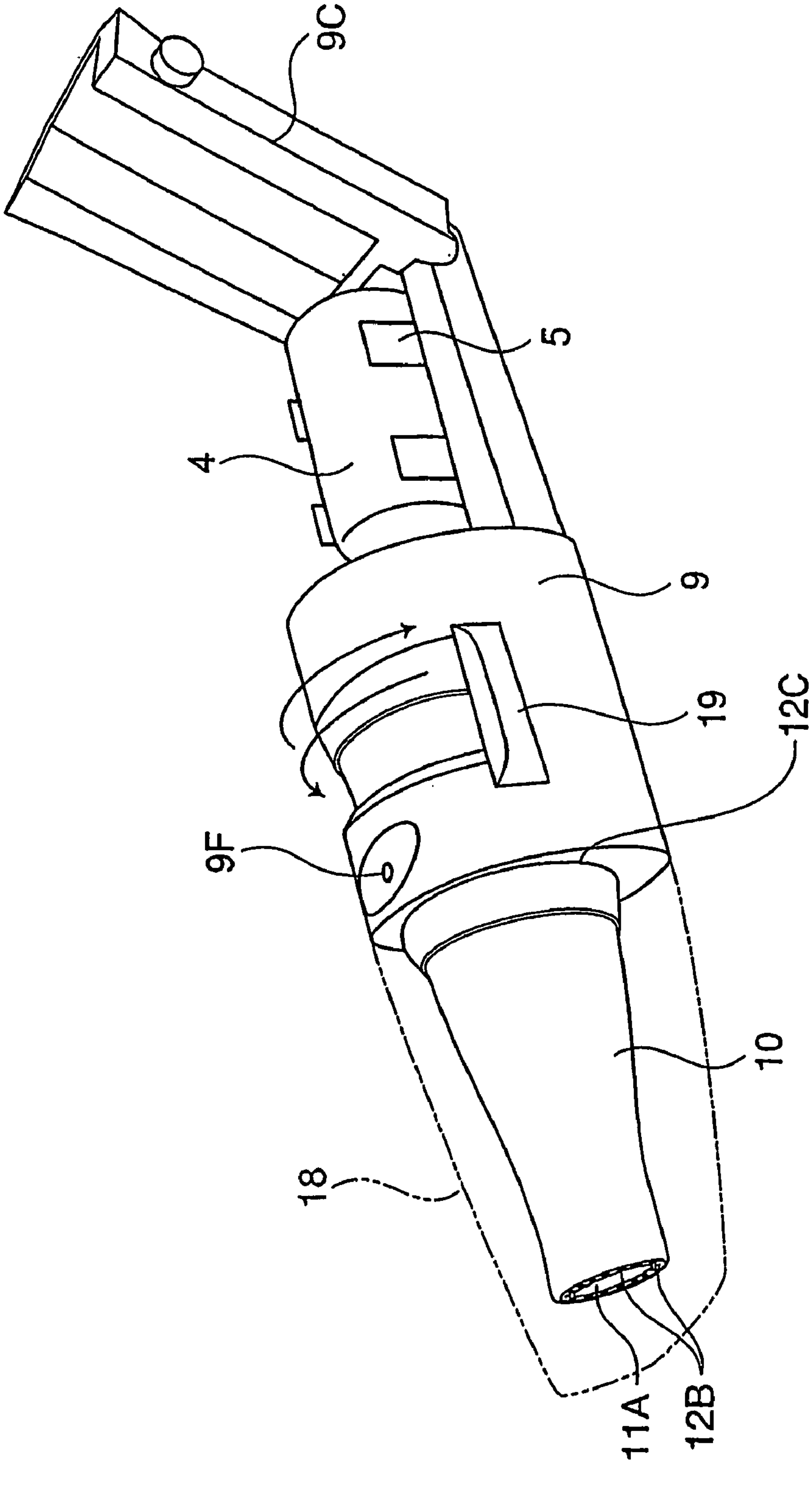
FIG. 21 is a perspective view illustrating an inhalation device according to another embodiment of the present invention.
Figure 22:
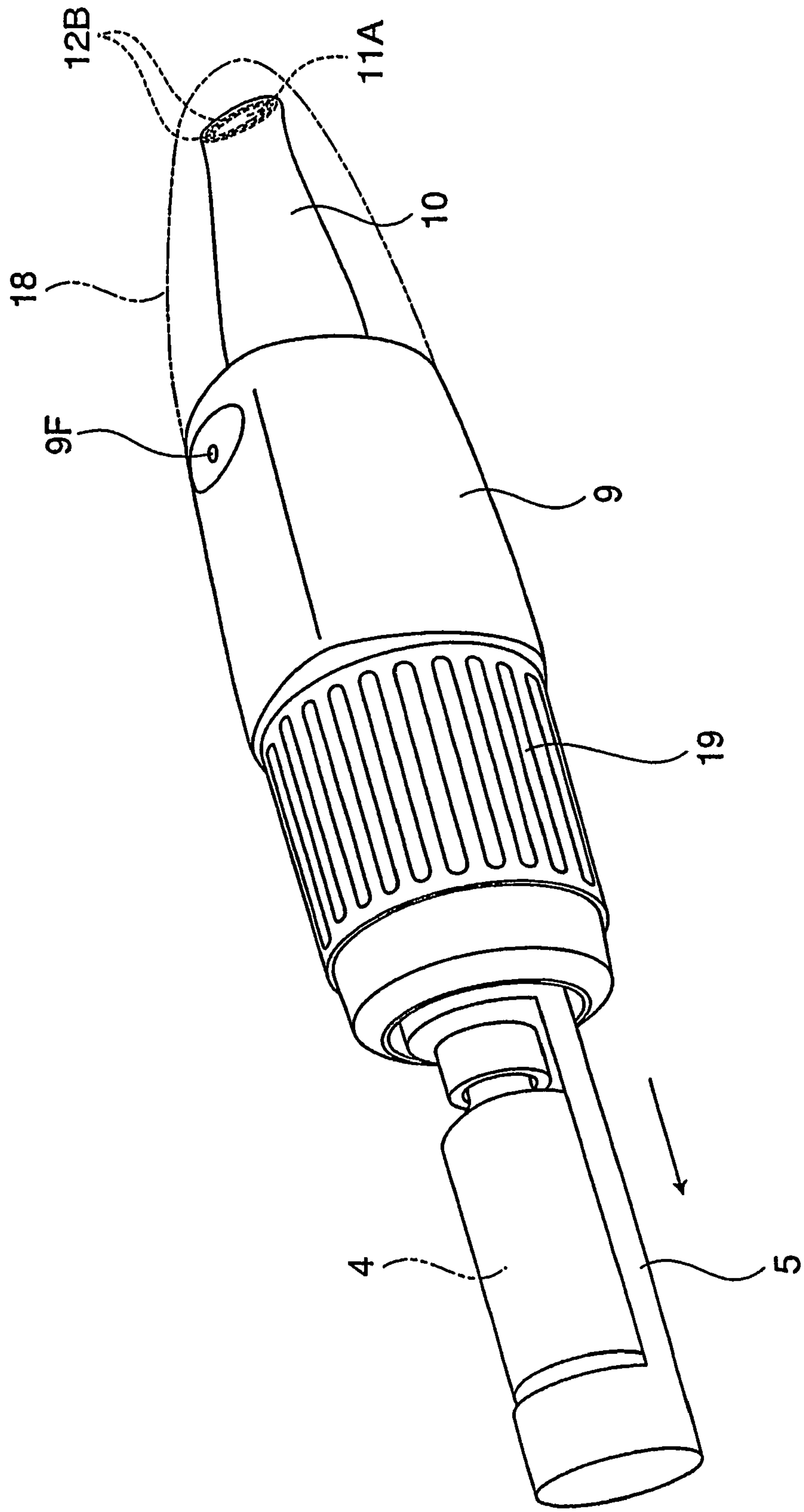
FIG. 22 is a perspective view illustrating a dry powder inhalation device according to another embodiment of the present invention.
Figure 23:
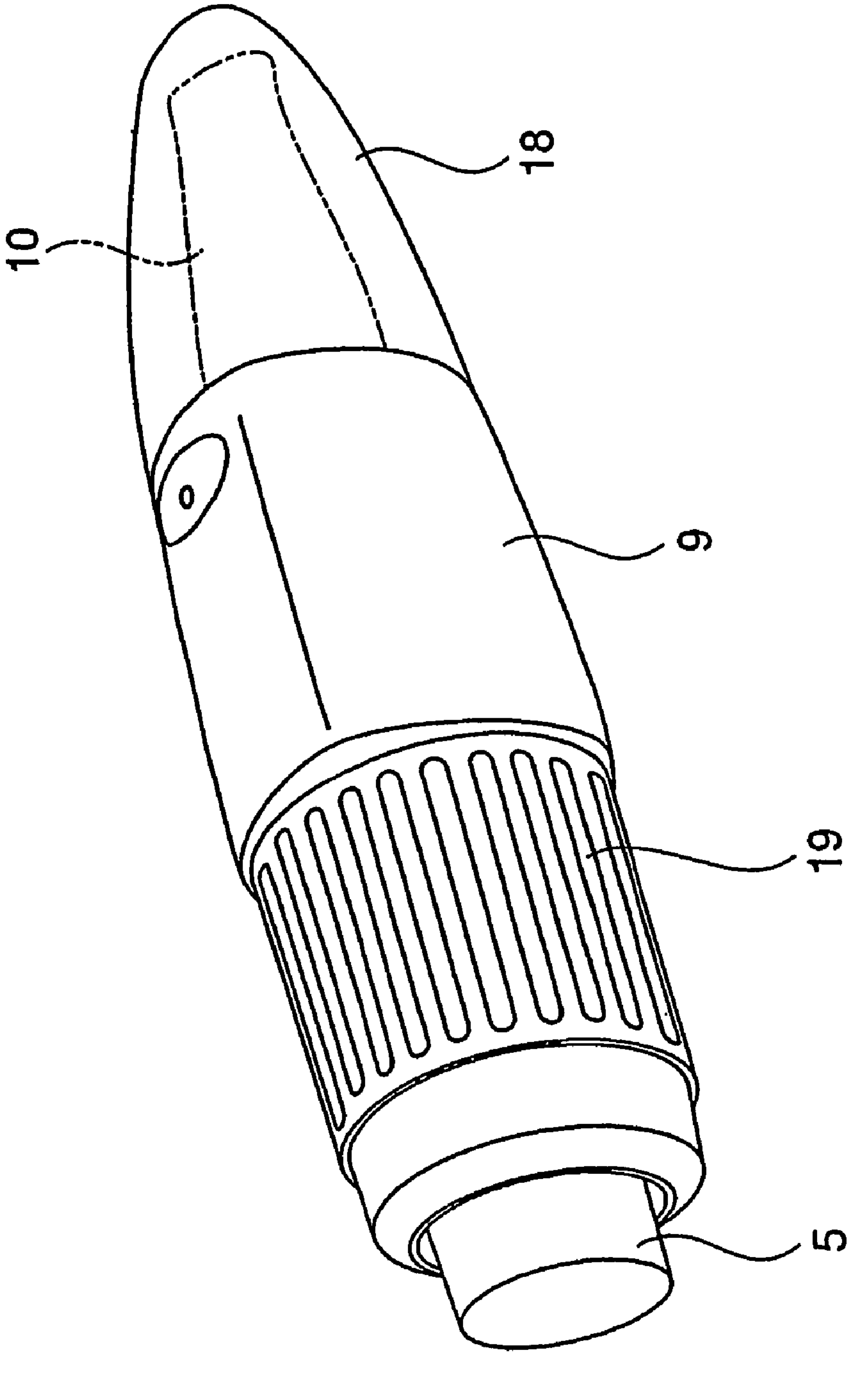
FIG. 23 is a perspective view illustrating a dry powder inhalation device according to another embodiment when not in use.

FIGS. 21 through 23 show examples of other embodiments. In the inhalation device shown in FIG. 21, an operating member 19 is arranged in such a way that it can be rotated in both forward and reverse circumferential directions of the housing 9 as shown by the arrows. The mechanism of the holder operating part, which is not shown in the drawing, is provided with a spiral groove and a follower that engages therewith; when the operating member 19 is rotated forward or reverse, this rotation is converted to a linear movement (back and forth movement) of the holder part 5 in the axial direction of the needle part 3. The rotation angle of the operating member 19 is substantially 180°. The inhalation devices shown in FIGS. 22 and 23 are rotatably provided with an annular operating member 19 at the housing 9. The mechanism of the holder operating part, which is not shown in the drawing, comprises a feed screw; when the operating member 19 is rotated, this rotation is converted to linear movement of the holder part 5 in the axial direction of the needle part 3. The holder part 5 can be withdrawn from the back of the housing 9. The other composite parts such as the mouthpiece 10, are the same as in the first embodiment.

Freeze-Dried Pharmaceutical Composition

A freeze-dried pharmaceutical composition is prepared in a non-powder dry form by pouring a solution containing a single effective dose of a drug into a vessel and then freeze-drying it as is. The non-powder-form freeze-dried pharmaceutical composition can be manufactured by a manufacturing method ordinarily used for freeze-dried preparations (freeze-dried pharmaceutical composition), such as an injection that is dissolved at the time of use by selecting a suitable composition (types and amounts of active ingredient and carrier used together with the active ingredient) such that the disintegration index of the freeze-dried pharmaceutical composition prepared is 0.015 or more, and the freeze-dried pharmaceutical composition can be made into fine particles down to a particle diameter suitable for transpulmonary administration by the impact of outside air introduced into the vessel.

The disintegration index in the present invention is a value particular to the freeze-dried pharmaceutical composition that can be obtained by measuring the composition according to the following method.

<Disintegration Index>

0.2 to 0.5 ml of a mixture containing target components that will constitute the freeze-dried composition is poured into a vessel having a trunk diameter of 18 mm or 23 mm, and is subjected to freeze-drying. Next, 1.0 ml of n-hexane is instilled gently down the wall of the vessel onto the non-powder-form freeze-dried pharmaceutical composition obtained. The mixture is agitated for about 10 seconds at 3,000 rpm, and is then put into a UV cell with an optical path length of 1 mm and an optical path width of 10 mm, and the turbidity is measured immediately at a measurement wavelength of 500 nm using a spectrophotometer. The measured turbidity is divided by the total amount (weight)) of the components constituting the freeze-dried pharmaceutical composition, and the value obtained is defined as the disintegration index.

Here, an example of the lower limit of the disintegration index of a freeze-dried pharmaceutical composition of the present invention can be given as the above-mentioned 0.015, preferably 0.02, more preferably 0.03, yet more preferably 0.04, still more preferably 0.05, and most preferably 0.1. Moreover, there is no particular restriction on the upper limit of the disintegration index of the freeze-dried pharmaceutical composition of the present invention, but an example can be given as 1.5, preferably 1, more preferably 0.9, yet more preferably 0.8, and still more preferably 0.7. The freeze-dried pharmaceutical composition of the present invention preferably has a disintegration index in a range including lower and upper limit selected as appropriate from the above, provided that the disintegration index is at least 0.015. Specific examples of the range of the disintegration index are 0.015 to 1.5, 0.02 to 1.0, 0.03 to 0.9, 0.04 to 0.8, 0.05 to 0.7 and 0.1 to 0.7.

Moreover, it is preferable to prepare the freeze-dried pharmaceutical composition of the present invention in a non-powder cake-like form through freeze-drying drying. In the present invention, 'non-powder-form freeze-dried pharmaceutical composition' means a dry solid obtained by freeze-drying a solution, and is generally called a 'freeze-dried cake'. However, even if cracks appear in the cake, the cake breaks into a plurality of large lumps, or part of the cake breaks into a powder during the freeze-drying process or during subsequent handling, this cake is still included as a non-powder-form freeze-dried pharmaceutical composition that is the subject of the present invention, provided the effects of the present invention are not impaired.

As described above, the freeze-dried pharmaceutical composition of the present invention has a disintegration index of 0.015 or more and a non-powder cake-like form and becomes fine particles having a mean particle diameter of 10 microns or less or a fine particle fraction of 10% or more from an air-generated impact having an air speed of at least 1 m/sec and an air flow rate of at least 17 ml/sec based on the specific property particular to the freeze-dried pharmaceutical composition characterized by the above-described disintegration index.

A preferable freeze-dried pharmaceutical composition is such that, from the above air-generated impact, the mean particle diameter becomes 10 microns or less and preferably 5 microns or less or the proportion of effective particles (fine particle fraction) of 10% or more, preferably 20% or more, more preferably 25% or more, still more preferably 30% or more, and most preferably 35% or more.

As described above, the air-generated impact applied to the freeze-dried pharmaceutical composition is not limited, as long as it is generated by air having an air speed of at least 1 m/sec and an air flow rate of at least 17 ml/sec. Specific examples of an air-generated impact include an impact generated by air having a speed of 1 m/sec or more, preferably 2 m/sec or more, more preferably 5 m/sec or more and still more preferably 10 m/sec or more. Here, there is no restriction on the upper limit of the air speed, but it is generally 300 m/sec, preferably 250 m/sec, more preferably 200 m/sec and yet more preferably 150 m/sec. The air speed is not limited and can be selected to be in a range with any of the above-described lower and upper limits; specifically, however, the ranges of 1 to 300 m/sec, 1 to 250 m/sec, 2 to 250 m/sec, 5 to 250 m/sec, 5 to 200 m/sec, 10 to 200 m/sec or 10 to 150 m/sec can be mentioned.

Examples of air-generated impact include those generated by air having an air flow rate of generally 17 ml/sec or more, preferably 20 ml/sec or more and more preferably 25 ml/sec or more. There is no particular restriction on the upper limit of the air flow rate; however, the air flow rate is generally 900 L/min, preferably 15 L/sec, more preferably 5 L/sec, yet more preferably 4 L/sec, and most preferably 3 L/sec. More specifically, the air flow rate is not limited and can be selected to be in a range with any of the above-described lower and upper limits; specifically, however, examples of such a range include 17 ml/sec to 15 L/sec, 20 ml/sec to 10 L/sec, 20 ml/sec to 5 L/sec, 20 ml/sec to 4 L/sec, 20 ml/sec to 3 L/sec and 25 ml/sec to 3 L/sec.

The inhalation device for transpulmonary administration of the present invention is configured as described above and provides various effects as described below.

As is evident from the above description, the inhalation device according to the present invention is provided with a mouthpiece having a mouth-side flow path communicating with an inhalation flow path, and an auxiliary flow path for directly inhaling outside air which does not communicate with the inhalation flow path and the mouth-side flow path, and is configured in such a way that outside air is directly introduced to the auxiliary flow path by the inhalation-induced pressure of a user (patient). Therefore, the auxiliary air does not collide with air containing the pulverized pharmaceutical composition, and thus the fine particles can be prevented from coalescing/agglomerating due to the flow of the auxiliary air. Auxiliary air containing no pharmaceutical composition is inhaled and thus, the air flow rate can be further increased. Therefore, the fine particles that are generated can be efficiently delivered to the lungs.

According to the inhalation device of the present invention, at least one of the mouth-side flow path or the inhalation flow path is provided with a divider having an orifice for reducing the diameter of the flow path by forming the step part. Thus, agglomerated masses of fine particles of the pharmaceutical composition passing through the mouth-side flow path of the mouthpiece can be dispersed.

Further, a plurality of dividers having an orifice are formed at appropriately spaced intervals, and thus agglomerated masses of the pharmaceutical composition can be further dispersed.

Moreover, fine particles can be prevented from coalescing/agglomerating due to the flow of the auxiliary air which occurs in the prior art, and further, agglomerated masses of fine particles of the pharmaceutical composition passing through the mouth-side flow path of the mouthpiece can be dispersed. Therefore, agglomerated masses of fine particles of the pharmaceutical composition can be prevented from entering the user's (patient's) mouth.

According to the inhalation device of the present invention, the pharmaceutical composition pulverized into fine particles by air-generated impact flows in the mouth-side flow path with surrounded by auxiliary air. Thus, the fine particles of the pharmaceutical composition are not dispersed by turbulent flow, and therefore fine particles of the pharmaceutical composition pass swiftly through the mouth-side flow path to reach the inside of lungs, which can avoid fine particles from adhering to throat. Moreover, the fine particles of the pharmaceutical composition can be prevented from adhering to the mouthpiece due to static electricity.

The outside air containing pulverized pharmaceutical composition pass through the orifice, and thereafter is surrounded by the auxiliary air. Thus, the auxiliary air is prevented from disturbing by the orifice.

Moreover, the flow-path length of the orifice is formed to be elongated to the air discharge direction of the mouth-side flow path. Therefore, the outside air containing the pharmaceutical composition in a turbulent flow is accelerated in the orifices to become a laminar flow. Thus, the outside air containing the pharmaceutical composition is easily surrounded by the auxiliary air.

Air containing the pulverized freeze-dried pharmaceutical composition is not mixed with the auxiliary air, and the divider car disperse agglomerated masses of fine particles of the pharmaceutical composition.

A check valve is provided for preventing the fine particles from flowing to the outside from the air inlet flow path even when the user (patient) mistakenly blows air instead of inhaling it.

The invention claimed is:

1. An inhalation device for transpulmonary administration comprising:

a housing;

a mouthpiece provided at one end of the housing;

a chamber accommodated in the housing containing a pharmaceutical composition in non-powder, freeze-dried form which is pulverized into fine particles by an air-generated impact for dispersal in air;

an air inlet flow path, for introducing to the chamber outside air and for injecting outside air toward the pharmaceutical composition to apply an air-generated impact to the pharmaceutical composition as a result of inhalation by a user;

an inhalation flow path having a suction port located inside the chamber to inhale the pulverized pharmaceutical composition; and an auxiliary flow path for inhaling outside air which does not flow via the chamber, the auxiliary flow path opening around the inhalation flow path in the direction of the air flow of the inhalation flow path such that the auxiliary air flowing out from the auxiliary flow path does not disturb the air flow of the inhalation flow path.

2. An inhalation device for transpulmonary administration according to claim 1, wherein:

the mouthpiece is provided with a mouth-side flow path which communicates with the inhalation flow path;

the auxiliary flow path for directly inhaling outside air does not communicate with the inhalation flow path and the mouth-side flow path; and the inhalation device for transpulmonary administration is configured such that air-generated impact is applied to the pharmaceutical composition by outside air which flows into the chamber by inhalation-induced pressure generated when a user inhales air, and the pulverized pharmaceutical composition is introduced to the mouth-side flow path, and at the same time outside air is directly introduced to the auxiliary flow path by the inhalation-induced pressure.

3. An inhalation device for transpulmonary administration according to claim 1, wherein:

the mouthpiece is provided with a mouth-side flow path which communicates with the inhalation flow path and a divider having an orifice in at least one of the mouth-side flow path or the inhalation flow path for reducing the diameter of the flow path by forming a step part; and the inhalation device for transpulmonary administration is configured such that air-generated impact is applied to the pharmaceutical composition by outside air which flows into the chamber by inhalation-induced pressure generated when a user inhales air so that the pulverized pharmaceutical composition is introduced to the inhalation flow path and the mouth-side flow path, and also passes through the orifice.

4. The inhalation device for transpulmonary administration according to claim 3, wherein a plurality of dividers each having an orifice are provided at spaced intervals.

5. The inhalation device for transpulmonary administration according to claim 1, wherein the mouthpiece is provided with a mouth-side flow path which communicates with the inhalation flow path, and the auxiliary flow path for inhaling outside air is not used for applying air impact to the pharmaceutical composition, and does not flow via the chamber, and furthermore allows the inhaled outside air to flow into the mouth-side flow path through an air outlet which opens into the mouth-side flow path, the air outlet opening in the air discharge direction of the mouth-side flow path and being formed in a ring shape along the inner circumferential wall surface of the mouth-side flow path; and the pharmaceutical composition is pulverized by air impact generated by outside air flowing into the chamber by inhalation-induced pressure that is generated when a user inhales air, and the pulverized pharmaceutical composition flows into the mouth-side flow path surrounded by outside air flowing into the mouth-side flow path from the ring-shaped air outlet.

6. The inhalation device for transpulmonary administration according to claim 5, further comprising a divider having an orifice for reducing the diameter of the flow path formed in the mouth-side flow path, wherein outside air containing the pulverized pharmaceutical composition passes through the orifice, and thereafter is surrounded by outside air flowing into the mouth-side flow path from the ring-shaped air outlet.

7. The inhalation device for transpulmonary administration according to claim 6, wherein the flow-path length of the orifice is elongated in the air discharge direction of the mouth-side flow path.

8. The inhalation device for transpulmonary administration according to claim 1, further comprising an unsealing member for releasing the sealed condition of a vessel provided by a sealing member, the vessel being accommodated in the chamber, containing a non-powder pharmaceutical composition which disperses in air by an air-generated impact, and sealed by the sealing member, wherein the vessel is unsealed by the unsealing member to establish communication between the chamber and the inside of the vessel; and air-generated impact is applied by inhalation-induced pressure to the pharmaceutical composition contained in the vessel.

9. The inhalation device for transpulmonary administration according to claim 1, further comprising a check valve to prevent the pulverized pharmaceutical composition from flowing from the air inlet flow path to the outside.

10. The inhalation device for transpulmonary administration according to claim 1, further comprising a divider for dividing the inhalation flow path, the divider having an orifice for reducing the diameter of the inhalation flow path and being located downstream of the air inlet port, wherein the housing comprises a main body formed cylindrically and a vessel provided detachably at the end of the main body;

the chamber is formed by the vessel for containing a pharmaceutical composition which is pulverized into fine particles by an air-generated impact for dispersal in air; and the inhalation flow path is formed from the inner side space of the main body, the mouth piece and the vessel, the inhalation flow path being for flowing outside air containing the fine particles of the pharmaceutical composition from the vessel-side toward the mouthpiece-side.

11. The inhalation device for transpulmonary administration according to claim 10, wherein the air inlet port is formed between the main body and the vessel by means of a notch provided at the end of the main body; and the auxiliary flow path is formed between the mouthpiece and the divider by means of a notch formed at the outer circumferential surface of the divider.

12. The inhalation device for transpulmonary administration according to claim 10, wherein the inhalation flow path has such a capacity that an air-generated impact can be applied to the pharmaceutical composition by outside air which is fed from the air inlet port into the inhalation flow path located upstream of the divider by an air inhalation of the user.

13. The inhalation device for transpulmonary administration according to claim 10, wherein the auxiliary flow path is provided with an air outlet which opens into the inhalation flow path of the mouthpiece; and the air outlet is provided at such a position that outside air flowing in from the air outlet is inhaled into the mouth of the user without passing through the orifice.

* * * * *